Figure 1:
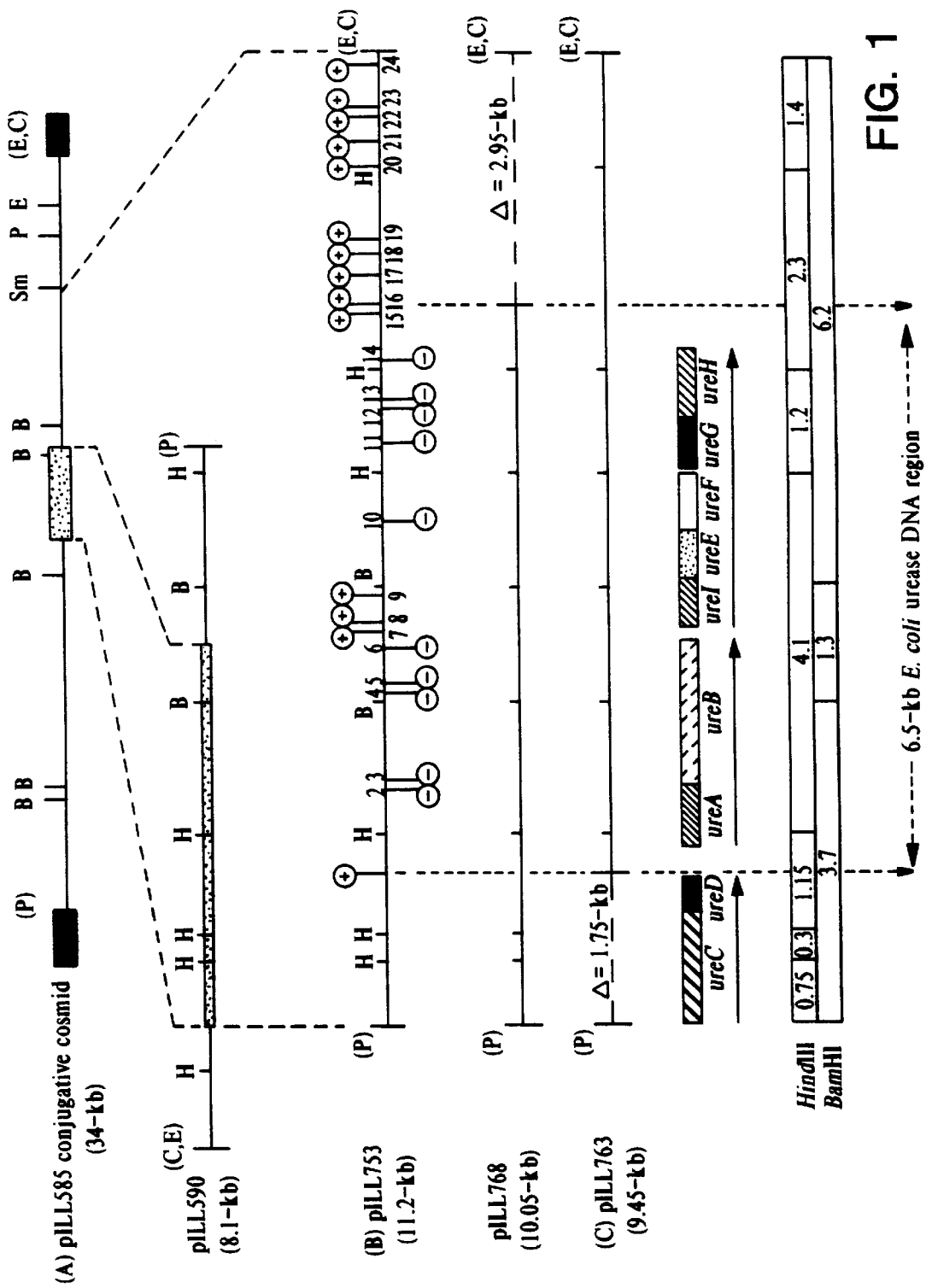

United States Patent [19]
Labigne et al.

[11] Patent Number: 6,027,878
[45] Date of Patent: Feb. 22, 2000

[54] **GENES OF *HELICOBACTER PYLORI* NECESSARY FOR THE REGULATION AND MATURATION OF UREASE AND THEIR USE**

[75] Inventors: Agnés Labigne, Bures Sur Yvette; Valérie Cussac; Richard Ferrero, both of Paris, all of France

[73] Assignees: Institut Pasteur; Inistitut National de la Sante et de la Recherche Medicale, both of France

[21] Appl. No.: 08/472,285

[22] Filed: Jun. 7, 1995

Related U.S. Application Data

[62] Division of application No. 08/211,312, filed as application No. PCT/FR92/00921, Oct. 2, 1992.

[30] Foreign Application Priority Data

Oct. 3, 1991 [FR] France ................................ 91 12198

[51] Int. Cl.$^7$ .............................. C12Q 1/68; C12P 19/34; C07H 21/02; C07H 21/04
[52] U.S. Cl. ......................... 435/6; 435/91.2; 435/240.2; 435/320.1; 435/252.3; 536/22.1; 536/23.1; 536/24.3; 536/24.31; 536/24.32; 536/24.33
[58] Field of Search ................................. 536/22.1, 23.1, 536/24.3, 24.31, 24.32, 24.33; 435/6, 91.2, 320.1, 240.2, 252.3

[56] References Cited

FOREIGN PATENT DOCUMENTS

| | | |
|---|---|---|
| A 0367 644 | 5/1990 | European Pat. Off. |
| 0 745 674 | 5/1996 | European Pat. Off. |
| WO 91/09049 | 6/1991 | WIPO |
| WO 96 33732 | 10/1996 | WIPO |
| WO 96 40893 | 12/1996 | WIPO |

OTHER PUBLICATIONS

V. Cussac et al., "Expression of Helicobacter pylori Urease Activity in *Escherichia coli* Host Strains". Society for Microbial Ecology and Disease, vol. 4(S), Oct. 1991, p. S139, Abstract H4–4.

V. Cussac et al., Expression of Helicobacter pylori Urease Genes in *Escherichia coli* Grown under Nitrogen–Limiting Conditions, Journal of Bacteriology 174(8):2466–2473 (Apr. 1992).

R. Ferrero et al., "Construction of Urease Deficient Mutants of Helicobacter pylori By Allelic Exchange", Society for Microbial Ecology and Disease, vol. 4(S), Oct. 1991, p. S139, Abstract H4–4.

A. Labigne et al., Bull. Acad. Natle. Med. 175(6):791–802 (1991).

T. Sugiyama et al., "A Novel Enzyme Immunoassay for Serodiagnosis of Helicobacter pylori infection", Gastroenterology 101:77–83 (1991).

Clayton et al, "Nucleotide sequence of two genes from helicobacter pylori encoding urease subunits", Nucleic Acids Res. 18(2):362, 1989.

Holbrook et al, "DNA sequence of the 5' flanking region of the human interleukin 2 gene: homologies with adult T cell leukemia virus", Nucleic Acids Res. 12(12):5005–5013, 1984.

Vasantha et al, "Fusion of pro region of subtilisin to staphlococcal protein A and its secretion by Bacillus subtilis", Gene 49:23–28, 1986.

Mulrooney et al, "Sequence of the Klebsiella aerogenes urease genes and evidence of accessory proteins facilitating nickel incorporation", J. Bacteriol. 172(10):5837–5843, Oct. 1990.

Skinner et al, "Coronavirus JHM: nucleotide sequence of the mRNA that encodes nucleocapsid protein", Nucleic Acids Res. 11(15):5045–5054, 1983.

Matthews et al, "Analytical strategies for the use of DNA probes", Anal. Biochem. 169–1–25, 1988.

Bogue et al, "Developmentally regulated expression of a sunflower 11S seed protein gene in transgenic tobacco", Mol. Gen. Genet. 222:49–57, 1990.

Weston et al, "Sequence of the short unique region, short repeats, and part of the long repeats of human cytomegalovirus", J. Mol. Biol. 192:177–208, 1986.

Chung et al, "Cloning and nucleotide sequence of the major capsid protein from lactococcus lactis sp. cremoris bacteriophage F4–1", Gene 101:121–125, 1991.

Park et al, "Sequence of MET protooncogene cDNA has features characteristic of the tyrosine kinase family of growth factor receptors", Proc. Natl. Acad. Sci. 84:6379–6383, Sep. 1987.

Mahbubani et al, "Detection of bacterial mRNA using polymerase chain reaction", Biotechniques 10(1):48–49, Jan. 1991.

Labigne–Roussel et al, "Gene transfer from *Escherichia coli* to camplyobacter species: Development of shuttle vectors for genetic analysis of camplyobacter jejuni", J. Bacteriol. 169(11):5320–5323, Nov. 1987.

*Primary Examiner*—W. Gary Jones
*Assistant Examiner*—Jeffrey Fredman
*Attorney, Agent, or Firm*—Finnegan, Henderson, Farabow, Garrett & Dunner, L.L.P.

[57] ABSTRACT

Oligonucleotide sequences are disclosed specific to *H. pylori* urease and useful as DNA probes and primers in the detection of *H. pylori* infection in humans. Also disclosed are methods of hybridization and amplification using these sequences.

40 Claims, 20 Drawing Sheets

```
1
A CTC TTT AGC ATT TTC TAG GA TTT TTT AGG AGC AAC GCT CTT AGA TCC TTA GTT TTT AGC
--leu phe ser ile phe AMB
                            31
61
TCT CTG ATT TTT TGT TTA TCA AAA AAT TGG GGG CTT TTT TTG TTT TTA TTT TTT GTC AAT
                                     91
121
TTA CTA TTT TTC TTT ATG ATT AGC TCA AGC AAC AAA AGT TAT TCG TAA GGT GCG TTT GTT
                                     151
181
GTA AAA ATT TTT GTT TGG AAG GAA AAG GCA ATG CTA GGA CTT GTA TTG TTA TAT GTT GGG
            SD               ureI     Met leu gly leu val leu leu tyr val gly
                                     211
241
ATT GTT TTA ATC AGC AAT GGG ATT TGC GGG TTA ACC AAA GTC GAT CCT AAA AGC ACT GCG
ile val leu ile ser asn gly ile cys gly leu thr lys val asp pro lys ser thr ala
                                     271
301
GTG ATG AAC TTT TTT GTG GGT GGG CTC TCC ATT ATT TGT AAT GTG GTT GTC ATC ACT TAT
val met asn phe phe val gly gly leu ser ile ile cys asn val val ile thr tyr
                                     331
361
TCC GCT CTC AAC CCT ACA GCC CCT GTA GAA GGT GCT GAA GAT ATT GCT CAA GTA TCA CAC
ser ala leu asn pro thr ala pro val glu gly ala glu asp ile ala gln val ser his
                                     391
421
CAT TTG ACT AAT TTC TAT GGG CCA GCG ACT GGG TTA TTG CTT CTT TTG TTT ACC TAC TTG TAT
his leu thr asn phe tyr gly pro ala thr gly leu leu phe gly phe thr tyr leu tyr
                                     451
```

FIG. 4A

```
481
GCG GCT ATC AAC CAC ACT TTT GGT TTG GAT TGG AGG CCC TAC TCT TGG TAT AGC TTA TTC
ala ala ile asn his thr phe gly leu asp trp arg pro tyr ser trp tyr ser leu phe 541
GTA GCG ATC AAC ACG ATT CCT GCT GCG ATT TTA TCC CAC TAT AGC GAT ATG CTT GAT GAC
val ala ile asn thr ile pro ala ala ile leu ser his tyr ser asp met leu asp asp 601
CAC AAA GTG TTA GGC ATC ACT GAA GGC GAT TGG TGG GCG ATC ATT TGG TTG GCT TGG GGT
his lys val leu gly ile thr glu gly asp trp trp ala ile ile trp leu ala trp gly 661
GTT TTG TGG CTT GCT ATC ACT GCT TTC ATT GAA AAC ATC TTG AAA ATC CCT TTA GGG AAA TTC ACT
val leu trp leu thr ala phe ile glu asn ile leu lys ile pro leu gly lys phe thr 721
CCA TGG CTT GCT ATC ATT GAG GGC ATT TTA ACC GCT TGG ATC CCT GCT TGG TTA CTC TTT
pro trp leu ala ile ile glu gly ile leu thr ala trp ile pro ala trp leu leu phe 781
ATC CAA CAC TGG GTG TGA GAT GAT CAT
ile gln his trp val OPA 782
TCC AAC ACT GGG TGT GAG ATG ATC ATA GAG CGT TTA ATA GGC AAT CTA AGG GAT TTA AAC
           Met ile ile glu arg leu ile gly asn leu arg asp leu asn
ureE
```

FIG. 4B

842
CCC TTG GAT TTC AGC GTG GAT TAT GTG GAT TTG GAA TGG TTT GAA ACG AGG AAA AAA ATC
pro leu asp phe ser val asp tyr val asp leu glu trp phe glu thr arg lys lys ile 871
GCT CGC TTT AAA ACC AGG CAA GGC ATA GCC GTA CGC CTT AAA GAC GCT CCC AAG
ala arg phe lys thr arg gln gly ile ala val arg leu lys asp ala pro lys 932
TTG GGT TTC TCT CAA GGA GAT ATT TTA TTT AAA GAA GAG AAG GAA ATT ATC GCC GTT AAT
leu gly phe ser gln gly asp ile leu phe lys glu glu lys glu ile ile ala val asn 992
ATC TTG GAT TCT GAA GTC ATT CAC ATC CAA GCT AAG AGC GTG GCA GAA GTA GCG AAA ATA
ile leu asp ser glu val ile his ile gln ala lys ser val ala glu val ala lys ile 1052
TGC TAT GAA ATA GGA AAC CGC CAT GCG GCT TTA TAC TAT GGC GAG TCT CAA TTT GAA TTT
cys tyr glu ile gly asn arg his ala ala leu tyr tyr gly glu ser gln phe glu phe 1112
AAA ACA CCA TTT GAA AAG CCC ACG CTA GCG TTA CTA GAA AAG CTA GGG GTT CAA AAT CGT
lys thr pro phe glu lys pro thr leu ala leu leu glu lys leu gly val gln asn arg 1172
GTT TTA AGT TCA AAA TTG GAT TCC AAA GAA CGC TTA ACC GTG AGC ATG CCC CAT AGT GAG
val leu ser ser lys leu asp ser lys glu arg leu thr val ser met pro his ser glu

1232

FIG. 4C

```
                                                         SD
1262
CCT AAT TTT AAG GTC TCA CTG GCG AGC GAT TTT AAA GTG GTC ATG AAA TAG AAA AAC AA
pro asn phe lys val ser leu ala ser asp phe lys val val met lys AMB 1292
1321
CAA ATG GAT AAA GGA AAA AGC GTG AAA AGC ATT GAA AAA AGC GTG GGT ATG CTC CCA AAA
F   Met asp lys gly lys ser val lys ser ile glu lys ser val gly met leu pro lys 1381
ACT CCA AAG ACA GAC AGC AAT GCT CAT GTG GAT AAT GAA TTT CTG ATT CTG CAA GTC AAT
thr pro lys thr asp ser asn ala his val asp asn glu phe leu ile leu gln val asn 1411
1441
GAT GCG GTG TTC CCC ATT GGA TCT CAT TCT TAC ACG TAT CCT TTT GGG CTT TTG GCT AGA AAC TTA
asp ala val phe pro ile gly ser his ser tyr thr tyr pro phe gly leu leu ala arg asn leu
                      1471

1501
CAT CCA GCA AAA AAG GTT ACT AAT AAA GAA AGC GCT TTA AAA TAT TTA AAA CTC ACC TAT GAA AGC GCT CTC
his pro ala lys lys val thr asn lys glu ser ala leu lys tyr leu lys leu thr tyr glu ser ala leu
                           1531

1561
TCT AGC CAG TTC CTT TAC ACG GAA ATG CTG AGC TTG AAA CTC ACC TAT GAA AGC GCT CTC
ser ser gln phe leu tyr thr glu met leu ser leu lys leu thr tyr glu ser ala leu
                      1591

1621
CAA CAA GAT TTA AAA AGG ATC TTA GGG GTT GAA GAA ATC ATT ACG CTA TCC ACA AGC CCC
gln gln asp leu lys arg ile leu gly val glu glu ile ile thr leu ser thr ser pro
                       1651
```

FIG. 4D

1681
ATG GAA TTG CGA TTA GCC AAT CAA AAG CTA GGC AAT CGT TTC ATT AAA ACC TTA CAA GCC
met glu leu arg leu ala asn gln lys leu gly asn arg phe ile lys thr leu gln ala 1741
ATG AAC GAA TTA GAC ATT GGC GCA TTT TTT AAC GCT TAC GCT CAA CAA ACC GAA GAC CCC
met asn glu leu asp ile gly ala phe phe asn ala tyr ala gln gln thr glu asp pro 1801
ACC CAT GCC ACT AGC TAT GGC GTT TTT GCG GCG AGT TTG GGG ATT GAA TTG AAA AAG GCT
thr his ala thr ser tyr gly val phe ala ala ser leu gly ile glu leu lys lys ala 1861
TTA AGG CAT TAT CTT TAT GCA CAA ACT TCT AAC ATG GTA ATT AAC TGC GTT AAA AGC GTC
leu arg his tyr leu tyr ala gln thr ser asn met val ile asn cys val lys ser val 1921
CCA CTA TCT CAA AAC GAT GGG CAA AAA ATC TTA TTG AGC TTG CAA AGC CCT TTT AAC CAG
pro leu ser gln asn asp gly gln lys ile leu leu ser leu gln ser pro phe asn gln 1981
CTC ATA GAA AAA ACC CTA GAC GAA CTA GAC CAT GAG AGT TTA TAC TCG CGC CTT TAT ATG TCT TGA ATT TTA
leu ile glu lys thr leu asp glu leu asp his glu ser leu tyr ser arg leu tyr met ser OPA 2041
GAC ATT AAG GCG ATG CAG CAT GAG AGT TTA TAC TCG CGC CTT TAT ATG TCT TGA ATT TTA
asp ile lys ala met gln his glu ser leu tyr ser arg leu tyr met ser OPA

FIG. 4E

```
       SD
2102  TCT CAA ATT GAA AGG AAT TTT ATG GTA AAA ATT GGA GTT TGT GGT CCT GTA GGA AGC GGT
       ureG                      Met val lys ile gly val cys gly pro val gly ser gly
2162                                                         2132

2162  AAA ACC GCC TTG ATT GAA GCT TTA ACG CGC CAC ATG TCA AAA GAT TAT GAC ATG GCG GTC
      lys thr ala leu ile glu ala leu thr arg his met ser lys asp tyr asp met ala val
                                                       2192

2222  ATC ACT AAT GAT ATT TAC ACG AAA GAA GAC GCA GAA TTT ATG TGT AAA AAT TCG GTG ATG
      ile thr asn asp ile tyr thr lys glu asp ala glu phe met cys lys asn ser val met
                                          2252

2282  CCA CGA GAG AGG ATC ATT GGC GTA GAA ACA GGA GGC TGT CCG CAC ACG GCT ATT AGA GAA
      pro arg glu arg ile ile gly val glu thr gly gly cys pro his thr ala ile arg glu
                                          2312

2342  GAC GCT TCT ATG AAT TTA GAA GCC GTA GAA GAA ATG CAT GGC CGT TTC CCT AAT TTG GAA
      asp ala ser met asn leu glu ala val glu glu met his gly arg phe pro asn leu glu
                                          2372

2402  TTG CTT TTG ATT GAA AGC GGA GGC AGT AAC CTT TCA GCG ACT TTC AAC CCA GAG CTA GCG
      leu leu leu ile glu ser gly gly ser asn leu ser ala thr phe asn pro glu leu ala
                                          2432

2462  GAC TTT ACG ATC TTT GTG ATT GAT GTG GCT GAG GGC GAT AAA ATC CCC AGA AAA GGC GGG
      asp phe thr ile phe val ile asp val ala glu gly asp lys ile pro arg lys gly gly
                                          2492
```

FIG. 4F

```
2522
CCA GGA ATC ACG CGT TCA GAC TTG CTT GTC ATC AAT AAG ATT GAT TTA GCC CCC TAT GTG
pro gly ile thr arg ser asp leu leu val ile asn lys ile asp leu ala pro tyr val 2582                                    2552
GGA GCC GAC TTG AAA GTC ATG GAA AGG GAT TCT AAA AAA ATC GCG GCG AAA AGC CCT TTA
gly ala asp leu lys val met glu arg asp ser lys lys ile ala ala lys ser pro leu 2642                                    2612
TTT TTA CCG AAT ATC CGC GCT AAA GAA GGT TTA GAC GAT GTG ATC GCT TGG ATC AAG CGC
phe leu pro asn ile arg ala lys glu gly leu asp asp val ile ala trp ile lys arg 2702                                    2672
AAC GCT TTA TTG GAA GAT TGA TGA ACA CTT
asn ala leu leu glu asp OPA 2701                    SD              2731
CAA CGC TTT ATT GGA AGA TTG ATG AAC ACT TAC GCT CAA GAA TCC AAG CTC AGG TTA AAA
     ureH                   Met asn thr tyr ala gln glu ser lys leu arg leu lys 2761                                    2791
ACC AAA ATA GGG GCT GAC GGG CGG TGC GTG ATT GAA GAC AAT TTT TTC ACG CCC CCC TTT
thr lys ile gly ala asp gly arg cys val ile glu asp asn phe phe thr pro pro phe 2821                                    2851
AAG CTC ATG GCG CCC TTT TAC CCT AAA GAC GAT TTA GCG GAA ATC ATG CTT TTA GCG GTA
lys leu met ala pro phe tyr pro lys asp asp leu ala glu ile met leu leu ala val
```

FIG. 4G

```
2881
AGC CCT GGC TTA ATG AAA GGC GAT GCA CAA GAT GTG CAA TTG AAC ATC GGT CCA AAT TGC
ser pro gly leu met lys gly asp ala gln asp val gln leu asn ile gly pro asn cys 2941                                                                    2911
AAG TTA AGG ATC ACT TCG CAA TCC TTT GAA AAA ATC CAT AAC ACT GAA GAC GGG TTT GCT
lys leu arg ile thr ser gln ser phe glu lys ile his asn thr glu asp gly phe ala 3001                                    2971
AGC AGA GAC ATG CAT ATC GTT GTG GGG GAA AAC GCT TTT TTA GAC TTC GCG CCC TTC CCG
ser arg asp met his ile val val gly glu asn ala phe leu asp phe ala pro phe pro 3061                3031
TTA ATC CCC TTT GAA AAC GCG CAT TTT AAG GGC AAT ACC ACG ATT TCT TTG CGC TCT AGC
leu ile pro phe glu asn ala his phe lys gly asn thr thr ile ser leu arg ser ser 3121        3091
TCC CAA TTG CTC TAT AGT GAA ATC ATT GTC GCA GGG CGA GTG GCG CGC AAT GAG TTG TTT
ser gln leu leu tyr ser glu ile ile val ala gly arg val ala arg asn glu leu phe 3181    3151
AAA TTC AAC CGC TTG CAC ACC AAA ATC TCT ATT TTA CAA GAT GAG AAA CCC ATC TAT TAT
lys phe asn arg leu his thr lys ile ser ile leu gln asp glu lys pro ile tyr tyr 3241   3211
GAC AAC ACG ATT TTA GAT CCC AAA ACC ACC GAC TTA AAT AAC ATG TGC ATG TTT GAT GGC
asp asn thr ile leu asp pro lys thr thr asp leu asn asn met cys met phe asp gly
           3271
```

FIG. 4H

3301
TAT ACG CAT TAT TTG AAT TTG GTG CTG GTC AAT TGC CCC ATA GAG CTG TCT GGC GTG CGA
tyr thr his tyr leu asn leu val leu val asn cys pro ile glu leu ser gly val arg 3361
GGA TTG ATT GAA GAG AGC GAA GGA GTG GAT GGA GCC GTG AGT GAA ATC GCT AGT TCT CAT
gly leu ile glu glu ser glu gly val asp gly ala val ser glu ile ala ser ser his 3421
TTA TGC CTG AAA GCT TTA GCG AAA GGC TCA GAA CCC TTG TTG CAT TTA AGA GAA AAA ATC
leu cys leu lys ala leu ala lys gly ser glu pro leu leu his leu arg glu lys ile 3481
GCT CGC TTT ATC ACG CAA ACG ATT ACG CCA AAG GTT TAA AAA ACA CTT TAA AAA AGA TTA
ala arg phe ile thr gln thr ile thr pro lys val OCH

3541
TAC CCT TTA GTC TTT TTT AA

FIG. 4I

Anti-urease diluted 1:1,000

Human antiserum diluted 1:1,000

GENES OF *HELICOBACTER PYLORI* NECESSARY FOR THE REGULATION AND MATURATION OF UREASE AND THEIR USE

This is a Division of application Ser. No. 08/211,312 filed on Jul. 1, 1994, pending, which was filed as International Application No. PCT/FR92/00921 on Oct. 2, 1992.

*Helicobacter pylori* (also described by the expression *H. pylori*) is a Gram negative bacterium found exclusively nowadays at the surface of the stomach mucosa in man, and more particularly around the lesions of the craters due to gastric and duodenal ulcers. This bacterium was initially called *Campylobacter pyloridis* (Warren et al. (1983) Lancet 1. 1273–1275).

Like most bacteria, *H. pylori* is sensitive to a medium of acidic pH but can however tolerate acidity in the presence of physiological levels of urea (Marshall et al. (1990) Gastroenterol. 99: 697–702). By hydrolysing urea to carbon dioxide and ammonia which are released into the microenvironment of the bacterium, the urease of *H. pylori* is assumed to permit the survival of the bacterium in the acidic environment of the stomach. Recently, studies conducted on animal models have provided elements suggesting that urease is an important factor in the colonization of the gastric mucosa (Eaton et al. (1991) Infect. Immun 59: 2470–2475). Urease is also suspected of causing injury either directly or indirectly to the gastric mucosa.

*Helicobacter pylori* (*H. pylori*) is presently recognized as the etiological agent of antral gastritis, and appears to be one of the cofactors required for the development of ulcers. Furthermore it seems that the development of gastric carcinomas may be linked to the presence of *H. pylori*.

All of the strains isolated in the clinic from biopsies or gastric juice synthesize a very active urease, which is exposed at the surface of the bacterium and is one of the most immunogenic proteins of *H. pylori*. The urease is suspected of playing a role in the pathogenic process, a fact which has been confirmed by experiments performed on the pig which show that weakly producing urease strains obtained by chemical mutagenesis were incapable of colonizing the stomach of the pig. These results obtained after chemical mutagenesis do not make it possible to attribute with certainty the diminution of urease production to an inability to colonize the stomach, since other genes may be inactivated during generalized mutagenesis. Hence these are not controllable mutations and, consequently, this procedure has no real value in the creation of agents designed to diminish, and even prevent, the harmful effects of urease in the case of an infection by *H. pylori*.

In addition to this role in the colonization of the stomach, it has been shown that urease as well as the ammonia released might have a direct cytotoxic effect on epithelial cells and an indirect effect by inducing an inflammatory response which might be responsible for the gastric lesions.

The urease is hence one of the most important determinants of pathogenicity and the construction of isogenic strains of *H. pylori* specifically inactivated in the genes responsible for the expression of urease, whether they be structural genes or accessory genes, are of primary importance for defining the role of urease in the colonization step, and for use in the construction of strains which can be used to protect individuals in a vaccination process, for example by the construction of attenuated strains.

Hitherto the urease genes had been localized on a 34 kb fragment of the *H. pylori* chromosome and had been associated with a 4.2 kb region present in this fragment. Four genes designated by the terms ureA, ureB, ureC and ureD had been associated with this region of 4.2 kb. This region led to the production of a urease-positive phenotype when the DNA of 4.2 kb was transferred by the intermediary of a shuttle vector to *Campylobacter jejuni*.

However, the transformation of *E. coli* cells with the DNA of 4.2 kb previously described did not lead to the expression of urease activity in *E. coli*.

The inventors have succeeded in defining the elements which, both genetically and from the point of view of growth conditions, are necessary for the expression in *E. coli* of a urease activity such as that obtained in *H. pylori*. In this regard, they have established that the expression of urease in *E. coli* was dependent on both the activation of the nitrogen regulatory system of *E. coli* and the presence of accessory genes to the urease structural genes. They have identified and isolated several genes which will sometimes be designated subsequently by the expression urease "accessory genes" which permit the functional expression of urease in *E. coli* and specify the maturation and regulation of urease in *H. pylori*.

Hence the invention relates to a set of five novel determinant genes or which are at least likely to be implicated in the functional expression of urease in *H. pylori* and in *E. coli*, as well as each of these genes considered in isolation and independently of the other genes. It also relates to this set of genes, optionally modified, in combination with the urease structural genes designated by ureA, ureB, ureC and ureD and described in the publication (Labigne et al. (1991) J. Bacteriol. 173: 1920–1931).

Furthermore, the invention relates to novel agents for the in vitro detection of an infection due to *H. pylori*, as well as to compositions which can be used for protection against infection by *H. pylori* .

Hence the object of the invention is a nucleotide sequence (SEQ ID NO:1) characterized in that it is constituted by or in that it comprises at least one of the nucleic acid sequences corresponding to the genes called ureE, ureF, ureG, ureH, ureI and represented by the nucleotide sequences presented below (SEQ ID NO:1):

```
1                                31
A CTC TTT AGC ATT TTC TAG GA TTT TTT AGG AGC AAC GCT CTT AGA TCC TTA GTT TTT AGC
  --leu phe ser ile phe AMB 61    ←----------    ---------→   91
TCT CTG ATT TTT TGT TTA TCA AAA AAT TGG GGG CTT TTT TTG TTT TTA TTT TTT GTC AAT 121                              151
TTA CTA TTT TTC TTT ATG ATT AGC TCA AGC AAC AAA AGT TAT TCG TAA GGT GCG TTT GTT 181                    SD        211
GTA AAA ATT TTT GTT TGG AAG GAA AAG GCA ATG CTA GGA CTT GTA TTG TTA TAT GTT GGG
```

```
         ureI                   Met leu gly leu val leu leu tyr val gly 241                             271
ATT GTT TTA ATC AGC AAT GGG ATT TGC GGG TTA ACC AAA GTC GAT CCT AAA AGC ACT GCG
ile val leu ile ser asn gly ile cys gly leu thr lys val asp pro lys ser thr ala 301                             301
GTG ATG AAC TTT TTT GTG GGT GGG CTC TCC ATT ATT TGT AAT GTG GTT GTC ATC ACT TAT
val met asn phe phe val gly gly leu ser ile ile cys asn val val val ile thr tyr 361                             391
TCC GCT CTC AAC CCT ACA GGC CCT GTA GAA GGT GCT GAA GAT ATT GCT CAA GTA TCA CAC
ser ala leu asn pro thr ala pro val glu gly ala glu asp ile ala gln val ser his 421                             451
CAT TTG ACT AAT TTC TAT GGG CCA GCG ACT GGG TTA TTG TTT GGT TTC ACC TAC TTG TAT
his leu thr asn phe tyr gly pro ala thr gly leu leu phe gly phe thr tyr leu tyr 481                             511
GCG GCT ATC AAC CAC ACT TTT GGT TTG GAT TGG AGG CCC TAC TCT TGG TAT AGC TTA TTC
ala ala ile asn his thr phe gly leu asp trp arg pro tyr ser trp tyr ser leu phe 541                             571
GTA GCG ATC AAC ACG ATT CCT GCT GCG ATT TTA TCC CAC TAT AGC GAT ATG CTT GAT GAC
val ala ile asn thr ile pro ala ala ile leu ser his tyr ser asp met leu asp asp 601                             631
CAC AAA GTG TTA GGC ATC ACT GAA GGC GAT TGG TGG GCG ATC ATT TGG TTG GCT TGG GGT
his lys val leu gly ile thr glu gly asp trp trp ala ile ile trp leu ala trp gly 661                             691
GTT TTG TGG CTT ACC GCT TTC ATT GAA AAC ATC TTG AAA ATC CCT TTA GGG AAA TTC ACT
val leu trp leu thr ala phe ile glu asn ile leu lys ile pro leu gly lys phe thr 721                             751
CCA TGG CTT GCT ATC ATT GAG GGC ATT TTA ACC GCT TGG ATC CCT GCT TGG TTA CTC TTT
pro trp leu ala ile ile glu gly ile leu thr ala trp ile pro ala trp leu leu phe 781
ATC CAA CAC TGG GTG TGA GAT GAT CAT
ile gln his trp val OPA 782                             812
TCC AAC ACT GGG TGT GAG ATG ATC ATA GAG CGT TTA ATA GGC AAT CTA AGG GAT TTA AAC
           ureE      Met ile ile glu arg leu ile gly asn leu arg asp leu asn 842                             871
CCC TTG GAT TTC AGC GTG GAT TAT GTG GAT TTG GAA TGG TTT GAA ACG AGG AAA AAA ATC
pro leu asp phe ser val asp tyr val asp leu glu trp phe glu thr arg lys lys ile 902                             932
GCT CGC TTT AAA ACC AGG CAA GGC AAA GAC ATA GCC GTA CGC CTT AAA GAC GCT CCC AAG
ala arg phe lys thr arg gln gly lys asp ile ala val arg leu lys asp ala pro lys 962                             992
TTG GGT TTC TCT CAA GGA GAT ATT TTA TTT AAA GAA GAG AAG GAA ATT ATC GCC GTT AAT
leu gly phe ser gln gly asp ile leu phe lys glu glu lys glu ile ile ala val asn 1022                            1052
ATC TTG GAT TCT GAA GTC ATT CAC ATC CAA GCT AAG AGC GTG GCA GAA GTA GCG AAA ATA
ile leu asp ser glu val ile his ile gln ala lys ser val ala glu val ala lys ile 1082                            1112
TGC TAT GAA ATA GGA AAC CGC CAT GCG GCT TTA TAC TAT GGC GAG TCT CAA TTT GAA TTT
cys tyr glu ile gly asn arg his ala ala leu tyr tyr gly glu ser gln phe glu phe 1142                            1172
AAA ACA CCA TTT GAA AAG CCC ACG CTA GCG TTA CTA GAA AAG CTA GGG GTT CAA AAT CGT
lys thr pro phe glu lys pro thr leu ala leu leu glu lys leu gly val gln asn arg 1202                            1232
GTT TTA AGT TCA AAA TTG GAT TCC AAA GAA CGC TTA ACC GTG AGC ATG CCC CAT AGT GAG
val leu ser ser lys leu asp ser lys glu arg leu thr val ser met pro his ser glu 1262                            1292            SD
CCT AAT TTT AAG GTC TCA CTG GCG AGC GAT TTT AAA GTG GTC ATG AAA TAG AAA AAC AA
pro asn phe lys val ser leu ala ser asp phe lys val val met lys AMB 1321                            1351
CAA ATG GAT AAA GGA AAA AGC GTG AAA AGC ATT GAA AAA AGC GTG GGT ATG CTC CCA AAA
 F  Met asp lys gly lys ser val lys ser ile glu lys ser val gly met leu pro lys
```

-continued

```
1381                                  1411
ACT CCA AAG ACA GAC AGC AAT GCT CAT GTG GAT AAT GAA TTT CTG ATT CTG CAA GTC AAT
thr pro lys thr asp ser asn ala his val asp asn glu phe leu ile leu gln val asn 1441                                  1471
GAT GCG GTG TTC CCC ATT GGA TCT TAC ACG CAT TCT TTT GGG CTT TTG GCT AGA AAC TTA
asp ala val phe pro ile gly ser tyr thr his ser phe gly leu leu ala arg asn leu 1501                                  1531
CAT CCA GCA AAA AGG GTT ACT AAT AAA GAA AGC GCT TTA AAA TAT TTA AAA GCC AAT CTC
his pro ala lys lys val thr asn lys glu ser ala leu lys tyr leu lys ala asn leu 1561                                  1591
TCT AGC CAG TTC CTT TAC ACG GAA ATG CTG AGC TTG AAA CTC ACC TAT GAA AGC GCT CTC
ser ser gln phe leu tyr thr glu met leu ser leu lys leu thr tyr glu ser ala leu 1621                                  1651
CAA CAA GAT TTA AAA AGG ATC TTA GGG GTT GAA GAA ATC ATT ACG CTA TCC ACA AGC CCC
gln gln asp leu lys arg ile leu gly val glu glu ile ile thr leu ser thr ser pro 1681                                  1711
ATG GAA TTG CGA TTA GCC AAT CAA AAG GTA GGC AAT CGT TTC ATT AAA ACC TTA CAA GCC
met glu leu arg leu ala asn gln lys val gly asn arg phe ile lys thr leu gln ala 1741                                  1771
ATG AAC GAA TTA GAC ATT GGC GCA TTT TTT AAC GCT TAC GCT CAA CAA ACC GAA GAC CCC
met asn glu leu asp ile gly ala phe phe asn ala tyr ala gln gln thr glu asp pro 1801                                  1831
ACC CAT GCC ACT AGC T|AT GGC GTT TTT GCG GCG| AGT TTG GGG ATT GAA TTG AAA AAG GCT
thr his ala thr ser tyr gly val phe ala ala ser leu gly ile glu leu lys lys ala 1861                                  1891
TTA AGG CAT TAT CTT TAT GCA CAA ACT TCT AAC ATG GTA ATT AAC TGC GTT AAA AGC GTC
leu arg his tyr leu tyr ala gln thr ser asn met val ile asn cys val lys ser val 1921                                  1951
CCA CTA TCT CAA AAC GAT GGG CAA AAA ATC TTA TTG AGC TTG CAA AGC CCT TTT AAC CAG
pro leu ser gln asn asp gly gln lys ile leu leu ser leu gln ser pro phe asn gln 1981                                  2011
CTC ATA GAA AAA ACC CTA GAA CTA GAC GAA AGC CAC TTG TGC GCG GCA AGC GTT CAA AAC
leu ile glu lys thr leu glu leu asp glu ser his leu cys ala ala ser val gln asn 2041                                  2071
GAC ATT AAG GCG ATG CAG CAT GAG AGT TTA TAC TCG CGC CTT TAT ATG TCT TGA ATT TTA
asp ile lys ala met gln his glu ser leu tyr ser arg leu tyr met ser OPA 2102        SD                        2132
TCT CAA ATT GAA AGG AAT TTT ATG GTA AAA ATT GGA GTT TGT GGT CCT GTA GGA AGC GGT
    ureG              Met val lys ile gly val cys gly pro val gly ser gly 2162                                  2192
AAA ACC GCC TTG ATT GAA GCT TTA ACG CGC CAC ATG TCA AAA GAT TAT GAC ATG GCG GTC
lys thr ala leu ile glu ala leu thr arg his met ser lys asp tyr asp met ala val 2222                                  2252
ATC ACT AAT GAT ATT TAC ACG AAA GAA GAC GCA GAA TTT ATG TGT AAA AAT TCG GTG ATG
ile thr asn asp ile tyr thr lys glu asp ala glu phe met cys lys asn ser val met 2282                                  2312
CCA CGA GAG AGG ATC ATT GGC GTA GAA ACA GGA GGC TGT CCG CAC ACG GCT ATT AGA GAA
pro arg glu arg ile ile gly val glu thr gly gly cys pro his thr ala ile arg glu 2342                                  2372
GAC GCT TCT ATG AAT TTA GAA GCC GTA GAA GAA ATG CAT GGC CGT TTC CCT AAT TTG GAA
asp ala ser met asn leu glu ala val glu glu met his gly arg phe pro asn leu glu 2402                                  2432
TTG CTT TTG ATT GAA AGC GGA GGC AGT AAC CTT TCA GCG ACT TTC AAC CCA GAG CTA GCG
leu leu leu ile glu ser gly gly ser asn leu ser ala thr phe asn pro glu leu ala 2462                                  2492
GAC TTT ACG ATC TTT GTG ATT GAT GTG GCT GAG GGC GAT AAA ATC CCC AGA AAA GGC GGG
asp phe thr ile phe val ile asp val ala glu gly asp lys ile pro arg lys gly gly 2522                                  2552
CCA GGA ATC ACG CGT TCA GAC TTG CTT GTC ATC AAT AAG ATT GAT TTA GCC CCC TAT GTG
pro gly ile thr arg ser asp leu leu val ile asn lys ile asp leu ala pro tyr val
```

```
2582                                    2612
GGA GCC GAC TTG AAA GTC ATG GAA AGG GAT TCT AAA AAA ATC GCG GCG AAA AGC CCT TTA
gly ala asp leu lys val met glu arg asp ser lys lys ile ala ala lys ser pro leu 2642                                    2672
TTT TTA CCG AAT ATC CGC GCT AAA GAA GGT TTA GAC GAT GTG ATC GCT TGG ATC AAG CGC
phe leu pro asn ile arg ala lys glu gly leu asp asp val ile ala trp ile lys arg 2702
AAC GCT TTA TTG GAA GAT TGA TGA ACA CTT
asn ala leu leu glu asp OPA 2701           SD                       2731
CAA CGC TTT ATT GGA AGA TTG ATG AAC ACT TAC GCT CAA GAA TCC AAG CTC AGG TTA AAA
               ureH         Met asn thr tyr ala gln glu ser lys leu arg leu lys 2761                                    2791
ACC AAA ATA GGG GCT GAC GGG CGG TGC GTG ATT GAA GAC AAT TTT TTC ACG CCC CCC TTT
thr lys ile gly ala asp gly arg cys val ile glu asp asn phe phe thr pro pro phe 2821                                    2851
AAG CTC ATG GCG CCC TTT TAC CCT AAA GAC GAT TTA GCG GAA ATC ATG CTT TTA GCG GTA
lys leu met ala pro phe tyr pro lys asp asp leu ala glu ile met leu leu ala val 2881                                    2911
AGC CCT GGC TTA ATG AAA GGC GAT GCA CAA GAT GTG CAA TTG AAC ATC GGT CCA AAT TGC
ser pro gly leu met lys gly asp ala gln asp val gln leu asn ile gly pro asn cys 2941                                    2971
AAG TTA AGG ATC ACT TCG CAA TCC TTT GAA AAA ATC CAT AAC ACT GAA GAC GGG TTT GCT
lys leu arg ile thr ser gln ser phe glu lys ile his asn thr glu asp gly phe ala 3001                                    3031
AGC AGA GAC ATG CAT ATC GTT GTG GGG GAA AAC GCT TTT TTA GAC TTC GCG CCC TTC CCG
ser arg asp met his ile val val gly glu asn ala phe leu asp phe ala pro phe pro 3061                                    3091
TTA ATC CCC TTT GAA AAC GCG CAT TTT AAG GGC AAT ACC ACG ATT TCT TTG CGC TCT AGC
leu ile pro phe glu asn ala his phe lys gly asn thr thr ile ser leu arg ser ser 3121                                    3151
TCC CAA TTG CTC TAT AGT GAA ATC ATT GTC GCA GGG CGA GTG GCG CGC AAT GAG TTG TTT
ser gln leu leu tyr ser glu ile ile val ala gly arg val ala arg asn glu leu phe 3181                                    3211
AAA TTC AAC CGC TTG CAC ACC AAA ATC TCT ATT TTA CAA GAT GAG AAA CCC ATC TAT TAT
lys phe asn arg leu his thr lys ile ser ile leu gln asp glu lys pro ile tyr tyr 3421                                    3271
GAC AAC ACG ATT TTA GAT CCC AAA ACC ACC GAC TTA AAT AAC ATG TGC ATG TTT GAT GGC
asp asn thr ile leu asp pro lys thr thr asp leu asn asn met cys met phe asp gly 3301                                    3331
TAT ACG CAT TAT TTG AAT TTG GTG CTG GTC AAT TGC CCC ATA GAG CTG TCT GGC GTG CGA
tyr thr his tyr leu asn leu val leu val asn cys pro ile glu leu ser gly val arg 3361                                    3391
GGA TTG ATT GAA GAG AGC GAA GGA GTG GAT GGA GCC GTG AGT GAA ATC GCT AGT TCT CAT
gly leu ile glu glu ser glu gly val asp gly ala val ser glu ile ala ser ser his 3241                                    3451
TTA TGC CTG AAA GCT TTA GCG AAA GGC TCA GAA CCC TTG TTG CAT TTA AGA GAA AAA ATC
leu cys leu lys ala leu ala lys gly ser glu pro leu leu his leu arg glu lys ile 3481                                    3511            ←------------
GCT CGC TTT ATC ACG CAA ACG ATT ACG CCA AAG GTT TAA AAA ACA CTT TAA AAA AGA TTA
ala arg phe ile thr gln thr ile thr pro lys val OCH

3541           ------------→
TAC CCT TTA GTC TTT TTT AA
``` or any part of at least one of these nucleic acid sequences.

A nucleotide sequence according to the invention is constituted either by DNA or by RNA.

The invention also relates to a nucleotide sequence modified with respect to the nucleotide sequence described above by deletion, addition, substitution or inversion of one or more nucleotides such that the functional properties of the polypeptides encoded in these genes are either conserved or attenuated, or even deleted, in comparison with the properties of the polypeptides UreE, UreF, UreG, UreH or UreI SEQ ID NOS: 4–7 and 3 respectively such as expressed by H. pylori, or such that this sequence does not express a polypeptide in H. pylori.

According to a particular embodiment of the invention and in the context of the preceding definition, a nucleotide sequence is characterized in that it is constituted by or in that it comprises:

a) the set of nucleotide sequences corresponding to the genes called ureE, ureF, ureG, ureH, ureI and represented by the nucleotide sequences shown in FIG. 4 or, b) the set formed by the (variant) nucleotide sequences corresponding to these genes modified independently of each other such that the set of these variants codes for polypeptides having a functional homology with the polypeptides UreE, UreF, UreG, UreH or UreI such as expressed by *H. pylori* or, on the other hand, codes for modified peptides which attenuate or even suppress the functional properties of the polypeptides UreE, UreF, UreG, UreH or UreI such as expressed by *H. pylori*.

Fragments (nucleotide sequences) of the above nucleotide sequences are of interest for different reasons and as examples it is possible to define:

fragments of the above-mentioned sequences which have conserved the capacity to code for polypeptides having a functional homology with the polypeptides such as obtained by expression of a gene selected from ureE, ureF, ureG, ureH, ureI in *H. pylori*;

fragments coding for any part of the above polypeptides such as produced in *H. pylori*, and in particular coding for peptides or parts of polypeptides recognized by antibodies directed against *H. pylori* or capable of behaving as haptens or immunogens;

fragments of the above-mentioned sequences lacking the capacity to code for the polypeptides of *H. pylori* such as expressed by the genes ureE, ureF, ureG, ureH, ureI;

fragments coding for polypeptides or peptides having properties attenuated or even deleted in comparison with the properties of the polypeptides encoded in the genes ureE, ureF, ureG, ureH, ureI of *H. pylori*.

Such fragments have advantageously at least 15 nucleotides, and preferably at least 20 nucleotides.

The genes ureE, ureF, ureG, ureH, ureI are present on a *H. pylori* chromosome, these genes are so-called accessory genes with respect to the urease structural genes (ureA, ureB). In contrast to the structural genes, the accessory genes are not necessary for the formation of the enzyme urease. On the other hand, they are implicated in the functional expression of urease as expressed in *H. pylori* by means of regulatory and/or maturation agents affecting the urease formed. The urease is in fact expressed in the form of an inactive apoenzyme before undergoing a maturation step within *H. pylori*, a step which confers on it its functional enzymatic form.

Furthermore, the inventors have observed that the presence of these five accessory genes is essential to the expression of functional urease in *E. coli* cells previously transformed by the structural genes ureA, ureB, ureC and ureD.

Consequently, the identification of these genes and their nucleotide sequences makes it possible to contemplate agents for modulating the urease activity in *H. pylori* strains, in particular for preparing attenuated strains.

According to a first embodiment of the invention, interesting nucleotide sequences code for polypeptides which have a functional homology with the natural polypeptides UreE, UreF, UreG, UreH and UreI. This homology between polypeptides is estimated in terms of the capacity of these polypeptides to function within *H. pylori* like the natural polypeptides UreE, UreF, UreG, UreH and UreI and, consequently, to contribute to the formation of the functional urease from the apoenzyme.

This functional homology can be detected by implementing the following test: $10^9$ bacteria are resuspended in 1 ml of urea-indole medium and incubated at 37° C. The hydrolysis of the urea leads to the release of ammonia which, by raising the pH, leads to a colour change from orange to fuchsia.

On the other hand, in context of the invention it is possible to make use of nucleotide sequences corresponding to the set of the nucleotide sequences corresponding to the genes ureE, ureF, ureG, ureH, ureI, these sequences being modified so that the polypeptides for which they code no longer possess the capacity of the natural polypeptides to give rise to the production of a functional urease in *H. pylori* or, optionally, in another species. In this case an attempt is made to attenuate or suppress the functional properties of the natural polypeptides as expressed by *H. pylori*. It is considered that the functional properties are attenuated when the strain in which the nucleotide sequences according to the invention are inserted produce a non-pathogenic urease for example in the form of an apoenzyme. This pathogenicity can be evaluated by making use of the following test:

The implantation of the recombinant strain is assayed in the stomach of an animal, preferably the germ-free piglet, by using the procedure described by Eaton et al. (1991 Infect. Immun. 59: 2470–2475).

According to a first embodiment of the invention, a nucleotide sequence such as previously defined may be combined with the nucleotides sequences corresponding to the structural genes ureA and ureB which code for the urease subunits in *H. pylori*.

According to another embodiment of the invention, this nucleotide sequence is combined with the genes ureA, ureB, ureC and/or ureD which code for urease in *H. pylori*.

In this case the different genes may be localized on distinct replicons.

The invention also relates to the nucleotide sequences included in the context of the preceding definition and represented by one of the coding nucleotide sequences corresponding to the genes ureE, ureF, ureG, ureH, ureI. In this connection the invention relates in particular to the following sequences:

the ureE sequence corresponding to the nucleotides 800 to 1309 of the sequence shown in FIG. 4, or any fragment of this sequence provided that it hybridizes under stringent conditions, i.e. at 68° C. in 6×SSC Denhardt medium or at 37° C. in 5×SSC 50% formamide with the ureE sequence or with the sequence complementary to this sequence, the ureF sequence corresponding to the nucleotides 1324 to 2091 of the sequence shown in FIG. 4, or any fragment of this sequence provided that it hybridizes under stringent conditions, i.e. at 68° C. in 6×SSC Denhardt medium or at 37° C. in 5×SSC 50% formamide with the ureF sequence or with the sequence complementary to his sequence, the ureG sequence corresponding to the nucleotides 2123 to 2719 of the sequence shown in FIG. 4, or any fragment of this sequence provided that it hybridizes under stringent conditions, i.e. at 68° C. in 6×SSC Denhardt medium or at 37° C. in 5×SSC 50% formamide with the ureG sequence or with the sequence complementary to this sequence, the ureH sequence corresponding to the nucleotides 2722 to 3516 of the sequence shown in FIG. 4, or any fragment of this sequence provided that it hybridizes under stringent conditions, i.e. at 68° C. in 6×SSC Denhardt medium or at 37° C. in 5×SSC 50% formamide with the ureH sequence or with the sequence complementary to this sequence, the ureI sequence corresponding to the nucleotides 211 to 795 of the sequence shown in FIG. 4, or any fragment of this sequence provided that it hybridizes under stringent conditions, i.e. at 68° C. in 6×SSC Denhardt medium or at 37° C. in 5×SSC 50% formamide with the ureH sequence or with the sequence complementary to this sequence.

Reverse and complementary DNA sequences are called here "complementary sequences". The term "reverse" takes into account the restoration of the 5'-3' orientation of the nucleic acid, complementary by the nature of the nucleotides and with respect to a given sequence.

The invention also relates to a particular nucleotide sequence corresponding to the following sequence. SEQ ID NO:8

GCG AAA ATA TGC TAT GAA ATA GGA AAC CGC CAT

The invention also relates to any DNA sequence which comprises this nucleotide sequence.

The nucleotide sequences according to the invention which satisfy the preceding specifications may be included in the constitution of probes when they are labelled for example at their 5' and/or 3' end by a substance which can be detected. As markers, mention may be made of radioactive isotopes, enzymes, chemical or chemoluminescent labels, fluorochromes, haptens or antibodies, base analogues or even physical markers. These markers may optionally be bound to a solid support for example a particulate or membrane support, such as magnetic beads.

As a preferred marker mention may be made of radioactive phosphorus ($^{32}P$) incorporated at the 5' end of the sequence used as probe.

Advantageously a nucleotide probe according to the invention comprises any fragment of the genes described, for example fragments of about 45 nucleotides.

Preferred probes according to the invention are constituted by fragments derived from the ureH gene or preferably from the ureI gene.

Starting from the nucleotide sequences according to the invention, it is also possible to define primers which can be used for the in vitro detection of an infection due to H. pylori. A primer is characterized in that it comprises a nucleotide fragment such as that derived from a sequence previously described, comprising from about 18 to about 30 and preferably from about 25 to about 30 nucleotides. Such a primer can be used in gene amplification reactions, for example according to the polymerase chain reaction.

For use in an amplification procedure primers of the invention are taken in pairwise combinations so as to hybridize under specific conditions with the respective 5' and 3' ends of the nucleotide fragment to be amplified.

If the PCR procedure is used, the required conditions for the specific hybridization of the primers with the DNA to be detected are the conditions described in the applications EP 200363, 201184, 229701 and the temperature is calculated according to the formula SEQ ID NO:8

$$T(° C.)=[4(C+G)+2(A+T)-10]$$

in which A, T, C, G represent respectively the number of A, T, C, G nucleotides in the primers used.

The amplification procedures which can be used in the framework of the invention include the PCR (polymerase chain reaction) procedure described in the European patent applications of Cetus (No. 200363, 201184 and 229701) or also the "Qbeta replicase" procedure described in Biotechnology (Vol. Oct. 6, 1988)

Other nucleotide sequences according to the invention are sequences which hybridize under stringent conditions such as those defined above with a sequence defined in the preceding pages or a sequence complementary to these sequences.

The nucleotide sequences and the vectors of the invention may also be used for the expression of other genes or sequences of H. pylori or of other strains in H. pylori or in other hosts such as E. coli, the adenovirus.

In addition, the invention relates to a polypeptide characterized in that it corresponds to one of the polypeptides UreE, UreF, UreG, UreH or UreI shown in FIG. 4, to any part of at least one of these polypeptides. The invention relates in particular to any modified polypeptide provided that it exhibits a functional homology with the original polypeptide UreE, UreF, UreG, UreH or UreI such as expressed by H. pylori or, on the contrary, modified by deletion, addition, substitution or inversion of one or more amino acids in order to attenuate or even abolish its functional properties as regards the urease activity as expressed by H. pylori.

The polypeptides UreE, UreF, UreG, UreH or UreI are implicated particularly in the regulation and the maturation of the urease in H. pylori.

Another polypeptide according to the invention is that which is represented by the following sequence of 11 amino acids (SEQ ID NO:9)

Ala Lys Ile Cys Tyr Glu Ile Gly Asn Arg His

The polypeptides of the invention and in particular the polypeptide whose sequence is given above can be used for the production of monoclonal or polyclonal antibodies, or for the detection of antibodies in a biological sample infected by H. pylori.

Monoclonal antibodies can be prepared by the hybridoma procedure or by known procedures for the preparation of human antibodies.

These antibodies can also be prepared according to the procedure described by Marks et al. (J. Mol. Biol. 1991 222, 581–597).

The invention also relates to anti-idiotypic antibodies.

Antibodies against the sequence of the above 11 amino acids might be used in the context of a reaction blocking the maturation of urease.

In additions, the invention relates to the use of the monoclonal or polyclonal antibodies in compositions to treat a H. pylori infection.

The object of the invention is also recombinant vectors characterized in that they contain a DNA sequence of the invention. Such recombinant vectors may be for example cosmids or plasmids.

A particularly advantageous vector for carrying out the invention is characterized in that it is the plasmid pILL753 contained in E. coli HB101 deposited with the CNCM (Collection Nationale de Cultures de Microorganismes, Paris France) on Oct. 3, 1991 under the number I-1148.

Another particularly advantageous recombinant vector is characterized in that it is the plasmid pILL763 contained in E. coli HB101 deposited with the CNCM or Oct. 3, 1991 under the number I-1149.

The object of the invention is also a recombinant cell host (or recombinant cell strain), characterized in that it is transformed by a nucleotide sequence satisfying the specifications previously given. This cell host thus transformed must allow the expression of the nucleotide sequence of the accessory genes of urease, optionally modified in conformity with the preceding specifications.

A recombinant cell host is preferably a strain of *H. pylori* modified by one of the nucleotide sequences previously specified, and advantageously modified such that the products of the modified accessory genes which it expresses contribute to the attenuation of the effects of urease, in particular its pathogenic effects.

For example, such a recombinant strain may be obtained by mutation of the N6 strain of *H. pylori* deposited with the NCIMB (National collections of Industrial and Marine Bacteria Ltd) in Great Britain, on Jun. 26, 1992 under the Number NCIMB 40512, the mutation being made in at least one of the genes ureE, ureF, ureG, ureH, ureI, and/or in one or more of the structural genes, for example ureA or ureB.

It will be preferable to create in the frame work of the invention recombinant strains and in particular recombinant *H. pylori* strains whose urease activity is attenuated in conformity with the criteria previously specified.

Thus, particularly useful recombinant N6 strains are those which give rise to a urease-negative phenotype and comprise a mutant form of at least of one of the genes ureE, ureF, ureG, ureH, or ureI.

An inactivation of the ureI gene for example makes it possible to prepare urease-negative *H. pylori* strains. Similarly, certain mutations within ureI give rise to a urease-negative phenotype in *H. pylori*, whereas the ureA and ureB gene products are expressed. For example it is mutation No. 8 described in the examples.

Another particularly useful mutation, especially for the preparation of vaccinating strains and in particular vaccinating *H. pylori* strains is a mutation in the ureG gene. A recombinant *H. pylori* strain in which the ureG gene is mutated exhibits the following properties:

the strain thus mutated conserves its capacity to trigger an immune response;

the strain thus mutated lacks urease activity.

However, it is possible to transform other strains with the sequences of the invention. In particular, recourse will be had to *E. coli* in order to create mutations in the genes ureE, ureF, ureG, ureH, or ureI, after their prior insertion in this strain, for example through the intermediary of a plasmid. The genes thus mutated can then be introduced into another host cell, for example in *H. pylori* in order to make possible an allelic replacement and create a mutation.

It is to be noted that the deletion in the ureI gene in a recombinant *E. coli* cell according to the invention does not alter the urease phenotype provided that the other conditions for the expression of this phenotype are fulfilled.

Moreover, the recombinant *E. coli* strain can be used to produce the polypeptides UreE, UreF, UreG, UreH or UreI and purify them by means of standard procedures.

The recombinant strains of *H. pylori* with attenuated urease activity can also be used for the transport and expression of heterologous genes, for example cholera or salmonella genes.

Different procedures can be used to generate recombinant strains. For example, recourse will be had to the electroporation procedure such as described in the example of this application.

This electroporation procedure may optionally be modified by eliminating the step which consists of giving an electric shock to the cells to be transformed.

The invention suggests agents for protection against an infection due to *H. pylori*, in particular by the administration of immunogenic compositions containing a recombinant cell strain characterized by an attenuated urease activity. Such immunogenic composition can be used in human medicine.

An immunogenic composition may contain strains such as *H. pylori* cells whose urease activity is attenuated by insertion in the strain of a nucleotide sequence according to the invention bearing at least one sequence corresponding to the genes ureE, ureF, ureG, ureH, or ureI, optionally modified to diminish the urease activity.

Generally, it may be any host capable of producing an attenuated urease, for example by mutation of the nucleotide sequences of one or more of the genes ureA, ureB, ureC, ureD, ureE, ureF, ureG, ureH, or ureI or by expression of a truncated form of a polypeptide implicated in the structure, maturation or regulation of the urease.

The object of the invention is also a kit for the in vitro diagnosis of a *H. pylori* infection in a biological sample, characterized in that it comprises:

at least one pair of nucleotide primers meeting the above criteria, capable of hybridizing with the 5' and 3' ends of a specific nucleotide fragment of at least one nucleotide sequence corresponding to a gene selected from ureE, ureF, ureG, ureH, or ureI, reagents necessary for the extraction of the nucleic acids from the treated sample, reagents for carrying out the polymerization of the said nucleotide fragment starting from the nucleotide primers, in particular polymerases, in sufficient quantity to carry out the amplification of the fragment which it is desired to amplify, at least one nucleotide sequence which can be used as probe and which is capable of hybridizing with the amplified DNA fragment under defined conditions, optionally, agents to reveal the hybridization.

According to a particular embodiment of the invention, it is also possible to include in the kit:

an internal control of the amplification reaction for example constituted by a nucleic acid, optionally plasmid-borne, the said nucleic acid being easily capable of detection by hybridization, for example by the fact that it contains a gene for resistance to an antibiotic or owing to the fact that it is constituted by the N6 chromosomal DNA, the said fragment being additionally provided at these two ends with at least one amplification primer, these primers being selected or not from the primers of the invention, and a probe capable of hybridizing with the nucleic acid contained in the internal control, optionally, a reverse transcriptase to produce the cDNA from the RNA possibly present in the sample tested.

The presence of an internal control added to the sample makes it possible to detect the presence of "false negatives" among the samples. In fact, when the specific probe for the internal control does not detect an amplification product, the sample concerned probably contains an inhibitor of the Taq polymerase, which hinders the amplification of the DNA or cDNA of *H. pylori*. In this case different dilutions of the tested sample can make possible the detection of the presence of *H. pylori* nucleic acid.

When the internal control shows a positive reaction, a negative reaction by the test sample leads to the deduction that *H. pylori* is indeed absent.

It is noted that the primers incorporated into the internal control are not necessarily those of the invention. However, the choice of other primers may lead to reduced sensitivity.

As an example of a biological sample for the detection of a *H. pylori* infection in man, samples should be used such as biopsies, gastric juice or possibly saliva or stools.

This kit may also be used for the control of water pollution or foodstuffs control.

The invention also relates to a procedure for the in vitro diagnosis of an infection due to *H. pylori* in a defined biological sample, characterized in that it comprises the steps of:

a) placing the nucleic acid of the sample likely to contain *H. pylori*, under conditions rendering it accessible in the form of single stranded DNA or RNA, in contact with at least one pair of nucleotide primers according to the invention, the said primers being capable of hybridizing with the nucleic acid of *H. pylori* if it is present, and of initiating the synthesis of the elongation products of the said primers, each strand of the nucleotide sequence of *H. pylori* serving as matrix when it is matched with the primers;

b) separation of the strands of nucleic acids synthesized from their matrix;

c) repetition of the synthesis of the elongation product starting from each strand of nucleic acid present at the end of step b) and capable of hybridizing with the primers until amplification of the desired nucleic acid in sufficient quantity to be detected is obtained, d) placing of the product of step c) in contact with a nucleotide probe under conditions allowing the detection of the presence of the desired amplified nucleic acid;

e) detection of the hybridization products possibly formed. According to a preferred embodiment of the procedure for in vitro diagnosis defined above, the placing in contact of the test sample is preceded by treatment of the sample so as to extract nucleic acid from it.

According to another preferred embodiment the procedure comprises a step prior to the placing in contact with the primers consisting of the treatment of the nucleic acid of the sample with a reverse transcriptase to lead to the synthesis of cDNA from the RNA possible present in the test sample.

The invention also relates to a kit for the in vitro diagnosis of a *H. pylori* infection characterized in that it comprises:

a defined quantity of probes according to the preceding specification, a suitable medium for carrying out a hybridization reaction between the *H. pylori* nucleic acid and the probe, reagents for the detection of the hybrids possibly formed.

A procedure for the use of this kit and for the in vitro diagnosis of a *H. pylori* infection starting from a biological sample is characterized in that it comprises:

the placing in contact of the sample to be tested whose DNA and/or RNA has been previously made accessible, with a previously specified probe under conditions allowing the hybridization of the nucleic acid with the probe.

the detection of a possible hybridization reaction between the nucleic acid and the probe.

The nucleotide sequences of the invention can be obtained either by extraction of the nucleic acid from *H. pylori* and digestion with selected endonucleases and purification, or also by chemical synthesis.

As an example the phosphotriester method such as described by Narang, S. A. et al. in Meth. of Enzymol., 68, 90 (1979) may be mentioned for the synthesis of such fragments of nucleic acids.

Another method which can be used for the preparation of nucleotide fragments is the phosphotriester method as described by Brown E. L. et al in Meth. of Znzymol., 68, 109 (1979).

This preparation can also be carried out by an automated process for example by making use of diethylphosphoramidites as starting components and in this case the synthesis can be carried out according to the description of Beaucage et al., Tetrahedron Letters (1981), 22, 1859–1862.

Other advantages and properties of the invention will become apparent in the Examples which follow and in the Figures.

FIGURES

FIG. 1: Subcloning and transposon mutagenesis of pILL753.

A: Linear restriction map of the pILL585 hybrid cosmid and the pILL590 plasmid (Labigne et al.-1991). The grey boxes represent the DNA fragment required for the expression of the urease in *C. jejuni*.

B: Random insertion of the transposon MiniTn3-Km. The numbers (1 to 24) and the circles correspond to the insertion site of the transposon in pILL753; the (+) signs indicate that the transposon has not inactivated the expression of the urease whereas the (−) signs indicate that the expression of urease has been abolished.

C: Linear restriction map of the hybrid plasmids pILL763 and pILL768 generated by deletion (Δ) within pILL753. The localization of the genes (ureA to ureH) is indicated by rectangles. The length of the rectangles corresponds to the length of the DNA required to express the polypeptides. The arrows refer to the orientation of transcription. The number of boxes at the bottom of the figure indicates the size in kilobases of the restriction fragments. The numbers in brackets correspond to the size of the *H. pylori* DNA fragments inserted in one of the cloning vectors (pILL575, pILL550 or pILL570). B, BamHI; E, EcoRI; P, PstI; H, HindIII; C, ClaI; Sm, SmaI. The letters between parentheses indicate that the restriction sites belong to the vector.

Figure 2A:
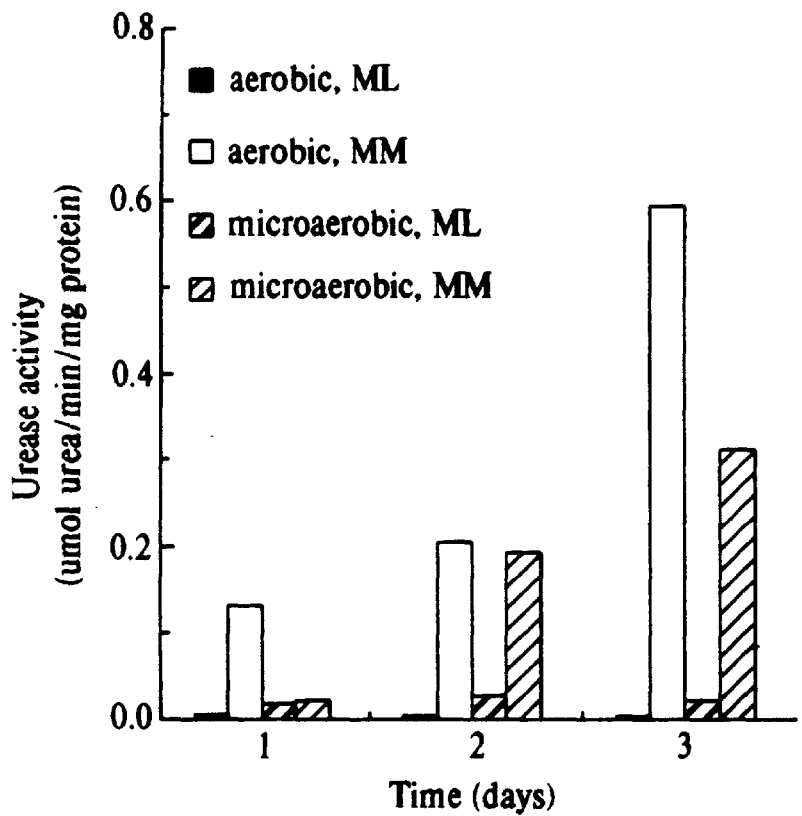
Figure 2B:
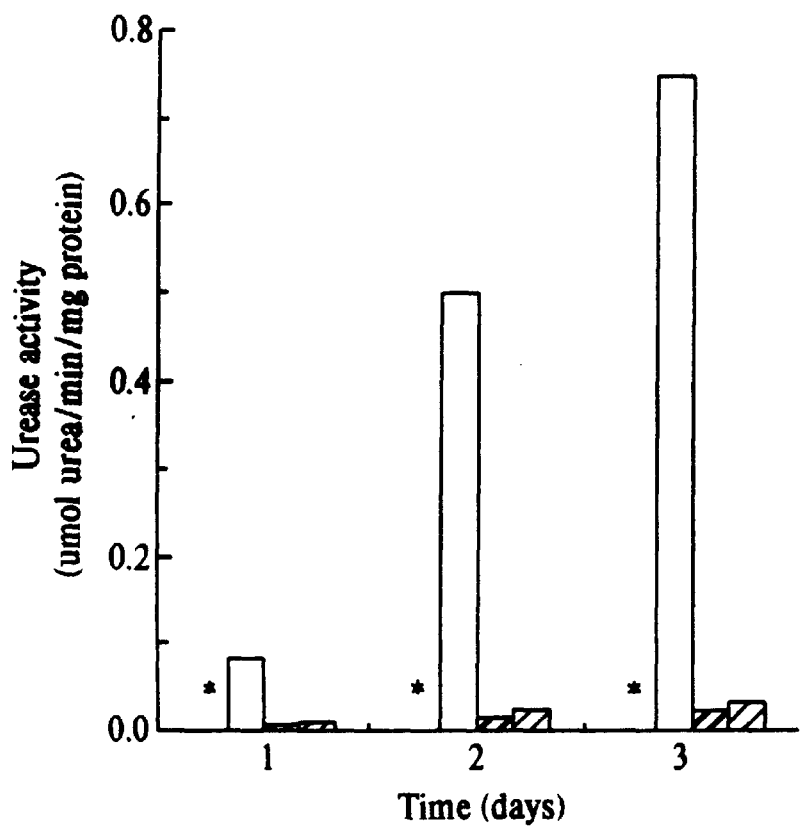

FIG. 2: Urease activity expressed by *E. coli* HB101 harbouring pILL753, as a function of time.

Plates prepared with either an L-agar medium (ML) or a minimal M9 medium supplemented with 10 mM L-arginine (MM) were each inoculated with a 100 μl aliquot of culture suspended ($10^8$ bacteria/ml) in 0.85% sterile NaCl. The plates were incubated aerobically or microaerobically at (A) 30° C. or (B) 37° C. and the activity measurements were made at the appropriate times. The asterisks indicate that no urease activity was detected.

Figure 3:
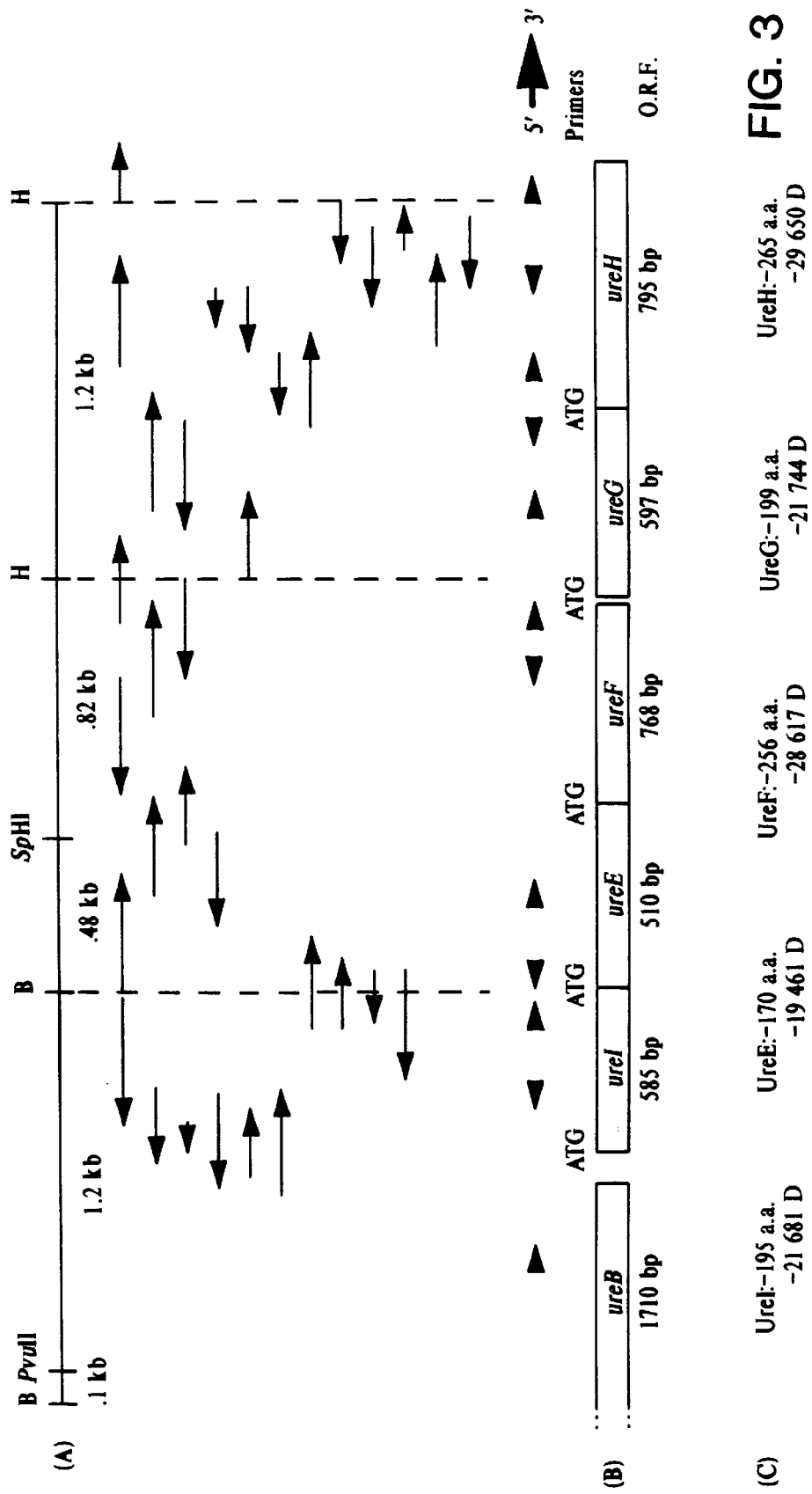

FIG. 3: DNA sequence of the accessory genes of *H. pylori* urease

A: Strategy for the sequencing of the accessory genes of the urease region of the hybrid plasmid pILL753. The arrows correspond to the sizes of the sequenced DNA fragments. The arrowheads represent the oligonucleotides used to carry out and confirm the oligonucleotide determination.

B: Schematic representation of the five open reading frames (ORFs) deduced from the nucleotide sequence analysis and the number of nucleotides. ATG corresponds to the initiation codon relative to each gene.

C: The sizes and calculated molecular masses of the five additional polypeptides of *H. pylori* urease are indicated.

FIG. 4: Nucleotide sequence (SEQ ID NO:1) of the accessory genes of *H. pylori* urease.

The numbers above the sequence indicate the position of the nucleotides. The predicted amino acid sequences (SEQ ID NOS:4–7 and 3, respectively) ordered sequentially, are: UreI (bp 211 to 795), UreE (bp 800 to 1309), UreF (bp 1324 to 2091), UreG (bp 2123 to 2719) and UreH (bp 2722 to 3516). The potential ribosome-binding sequences (Shine-Dalgarno, SD sites) are underlined. The boxed-in sequences correspond to the sequences of the promoter-like type (σ54) and the arrows above the sequence indicate the loop structures with the elements of a rhoindependent end-of-transcription signal (Rosenberg et al. (1979) Annu. Rev. Genet. 13: 319–359). The dotted lines under the amino acid sequence correspond to the DNA (ureI)—or ATP (ureG)—binding domain of the protein (Higgins et al (1985) EMBO J. 4: 1033–1040 and Pabo et al. (1984) Ann. Rev. Biochem. 53: 293–321).

Figure 5:
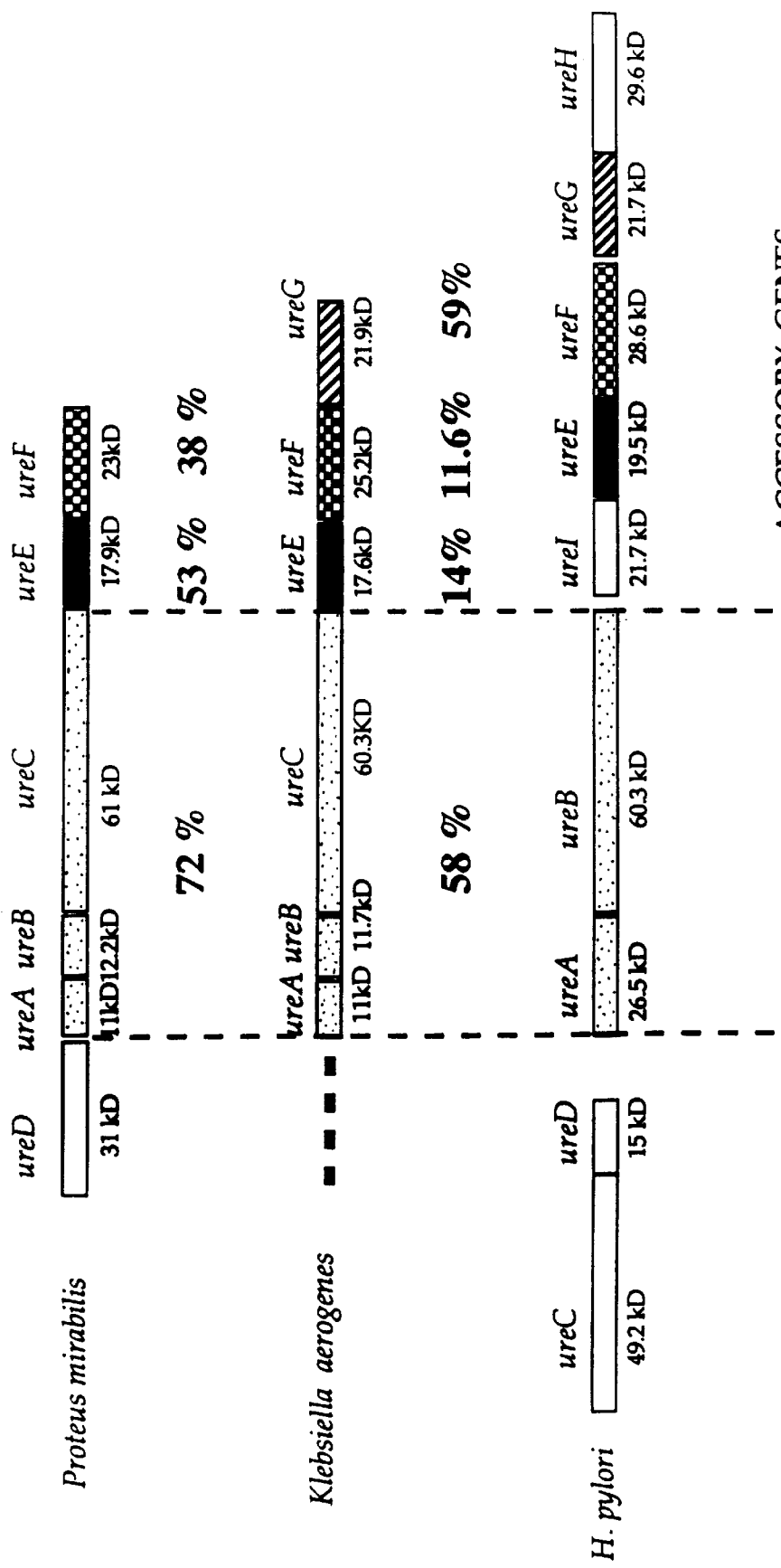

FIG. 5: Genetic organization of the urease operon

The relative positions of the genes coding for polypeptides associated with the urease operon of *P. mirabilis* (Jones et al. (1989) J. Bacteriol. 171: 6414–6422), *K. aerogenes* (Mulrooney et al.-1990) and *H. pylori* are shown. The percentages refer to the proportion of identical amino acids between two related genes. The white boxes represent the genes which are unique to the operon.

Figure 6A:
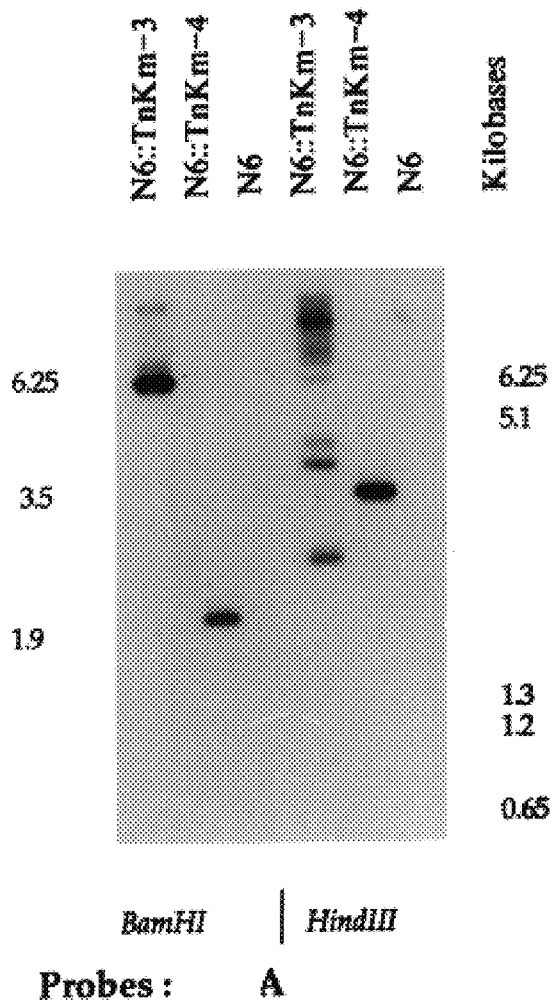
Figure 6B:
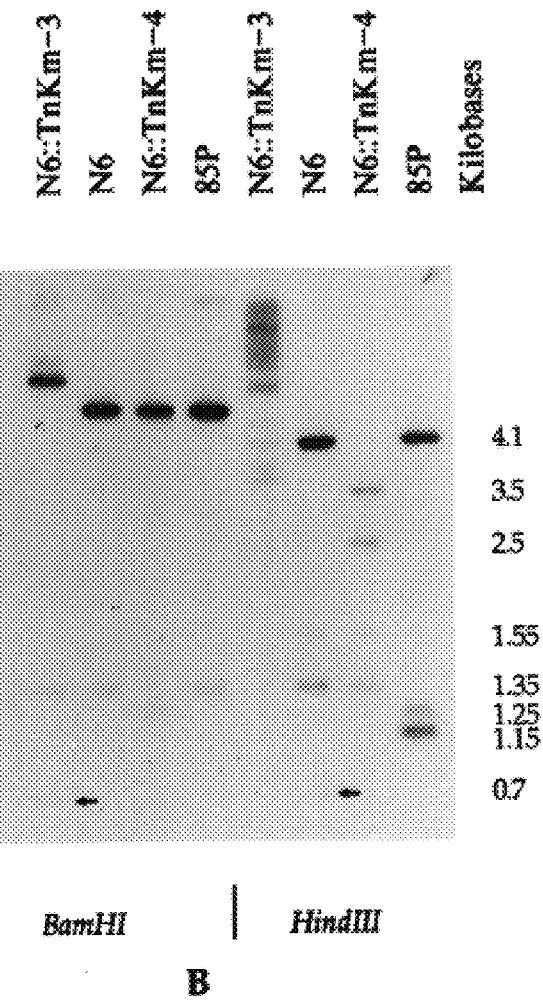
Figure 7:
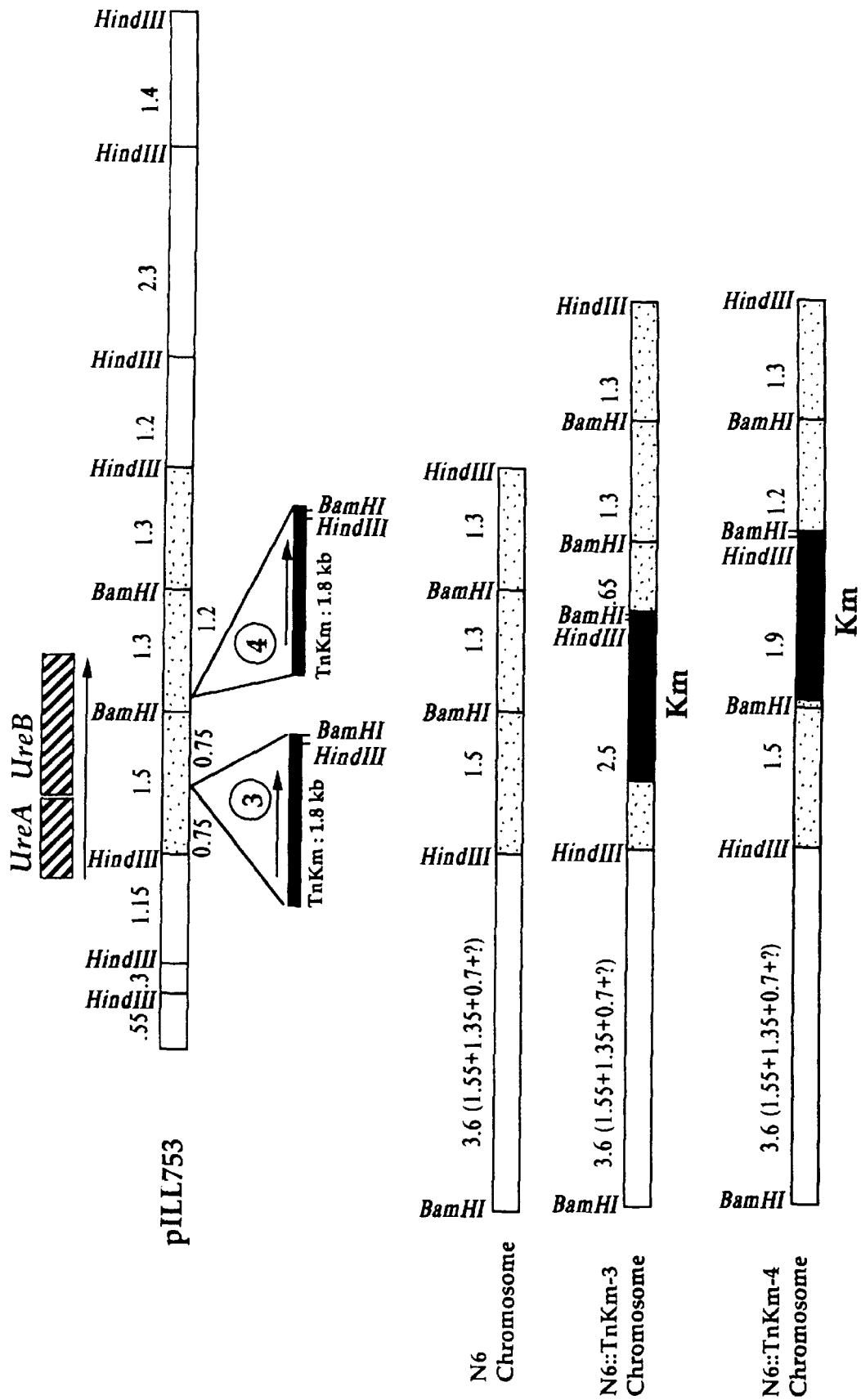

FIGS. 6 and 7: Analysis of the parental and mutant strains

Figure 8:
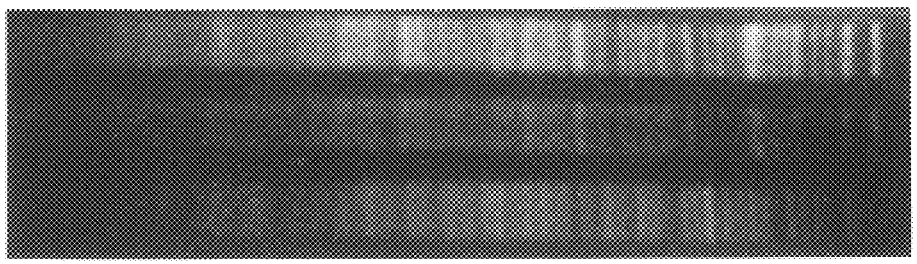

FIG. 8: Restriction profiles after enzymatic digestion of the total DNAs of the 85P, N6 and mutant N6 (urease⁻) strains.

Figure 9:
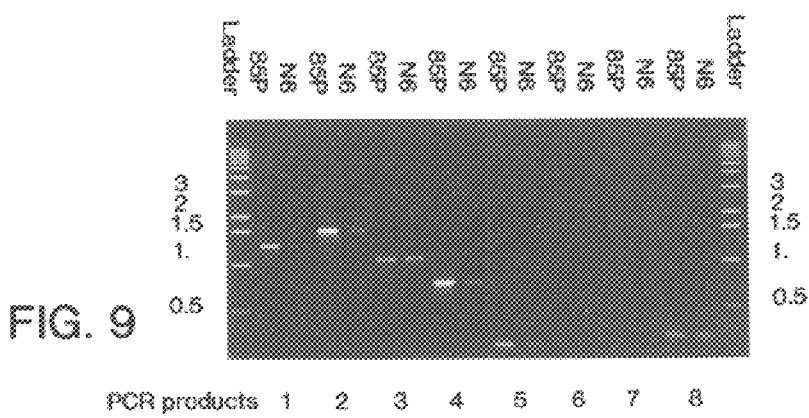
Figure 10:
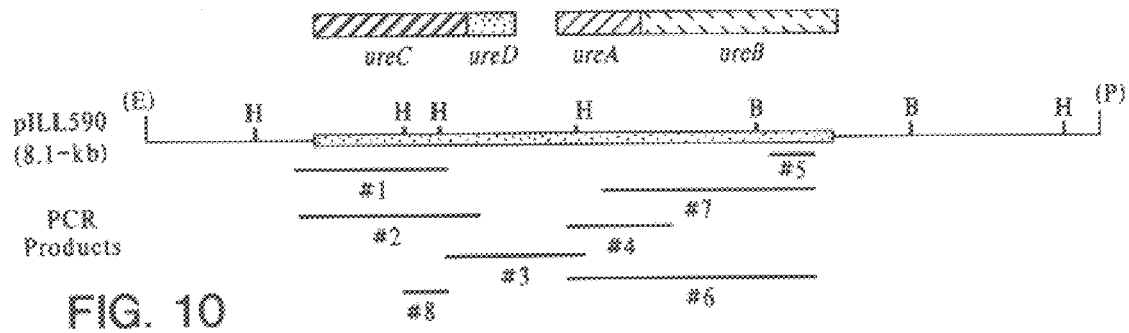

FIGS. 9 and 10: Genomic organization of the 4 ure genes in the genomes of the 85P and N6 strains. The specific DNA fragments were amplified starting from the chromosomal DNA extracted from the 85P and N6 isolates of *H. pylori* by using 8 pairs of primers in conformity with FIG. 10. The amplification products were separated by electrophoresis on 1.4% agarose gel. The values on each side of the gel correspond to the dimensions (in kilobases) on the 1 kb ladder used as standard.

Figures 11A, 11B:
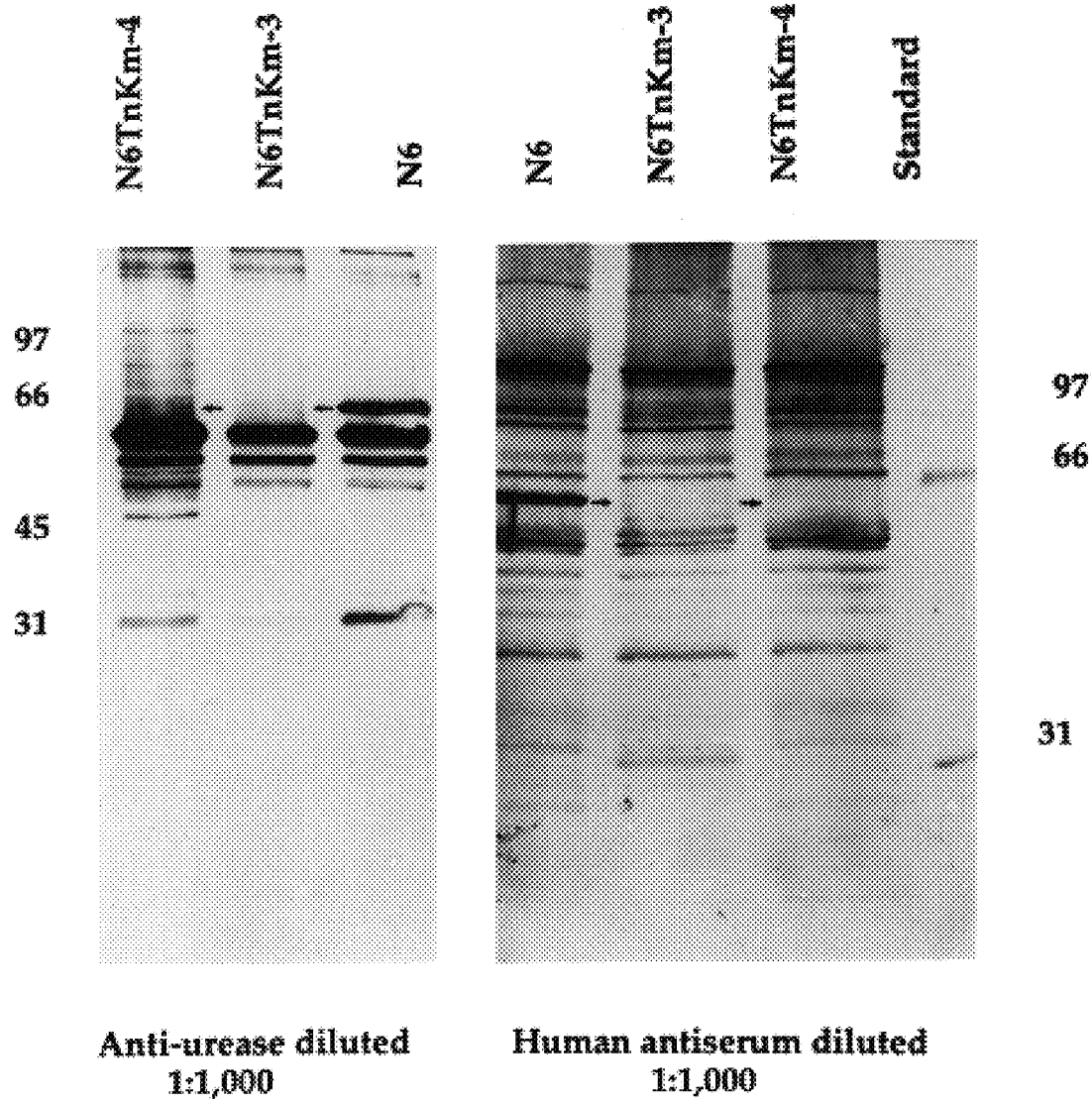

FIG. 11: Immunoblotting using antibodies

Figure 12:
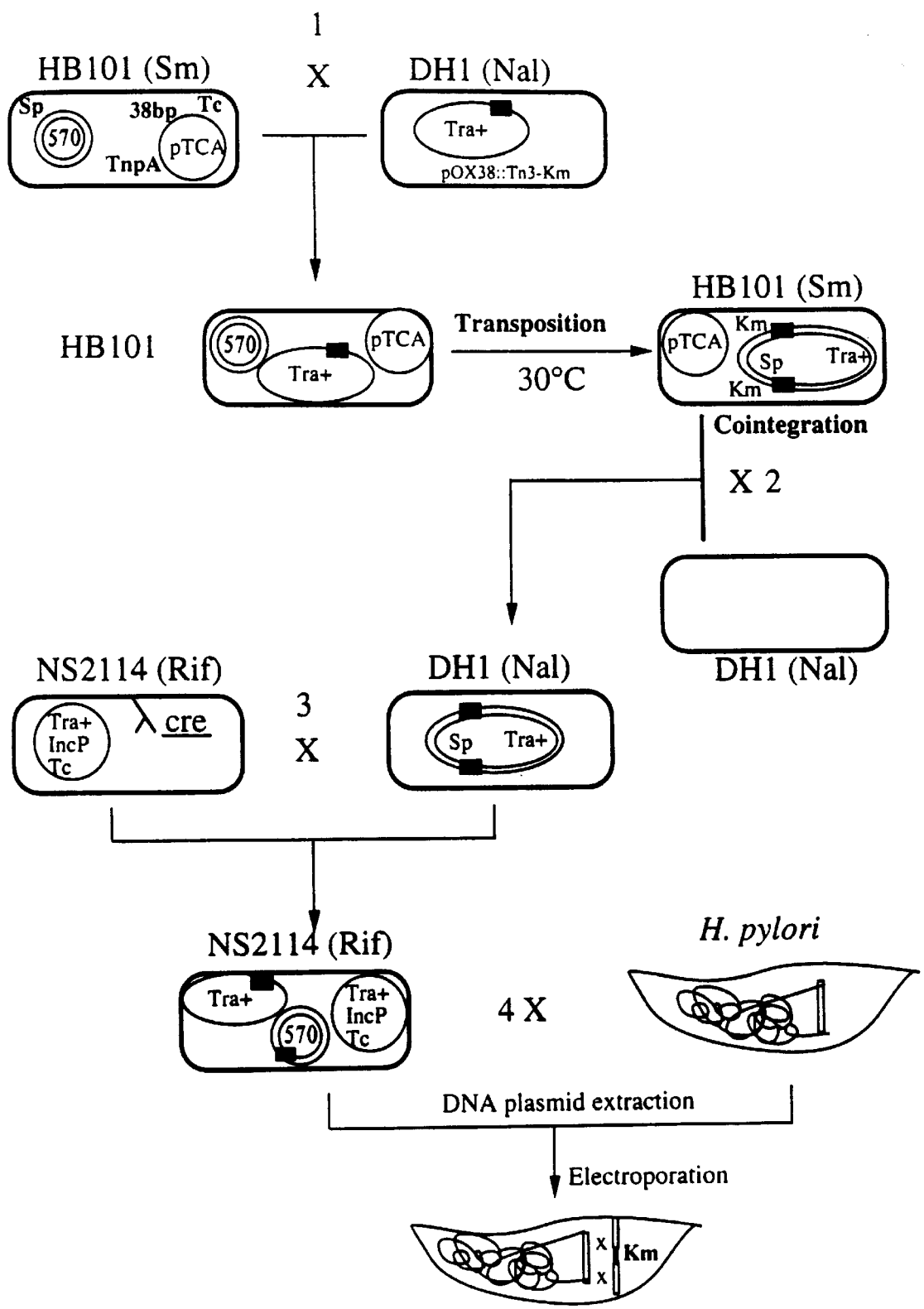

FIG. 12: Mutagenesis by transposon: schematic representation of four necessary consecutive steps for the construction of mutants in a *H. pylori* bacterium.

Conjugation 1: the transferable plasmid pOX38 of the IncF group harbouring the transposon MiniTn3-Km is introduced into *E. coli* HB 101 containing 1) the plasmid pTCA which expresses constitutively the transposase Tn3 (TnpA) and is immune to Tn3 owing to the presence of the sequence Tn3-38 bp and 2) the suicide conjugation vector containing the cloned fragment of *H. pylori* to be mutagenized. The kanamycin HB101 transconjugants are grown for 48 hours at 30° C. and the bacteria are conjugated with *E. coli* DH1 (Na1).

Conjugation 2: the cointegrates resulting from the transposition of MiniTn3-Km in the plasmid derived from pILL570 in the absence of resolvase are selected as conjugative kanamycin cointegrates in the DH1 cells.

Conjugation 3: the cointegrates are introduced into the strain NS2114 (Rif) harbouring the cre gene capable of producing a resolution by specific recombination of the cointegrate into two replicons, one consisting of the original donor of the transposon (pOX38-MiniTn3-Km) and the other consisting of the hybrid plasmid derived from pILL570 in which MiniTn3-Km has been inserted. The positive selection of the resolved forms of the cointegrates was obtained by selection of the N2114 transconjugants with kanamycin on a medium containing 300 μg/ml of kanamycin as well as 300 μg/ml of spectinomycin. The last step consisting of the introduction of the mutant DNA in *H. pylori* may be carried out by electroporating *H. pylori* with the plasmid DNA extracted from *E. coli* NS2114 (reference strain) obtained in step 3.

Figure 13:
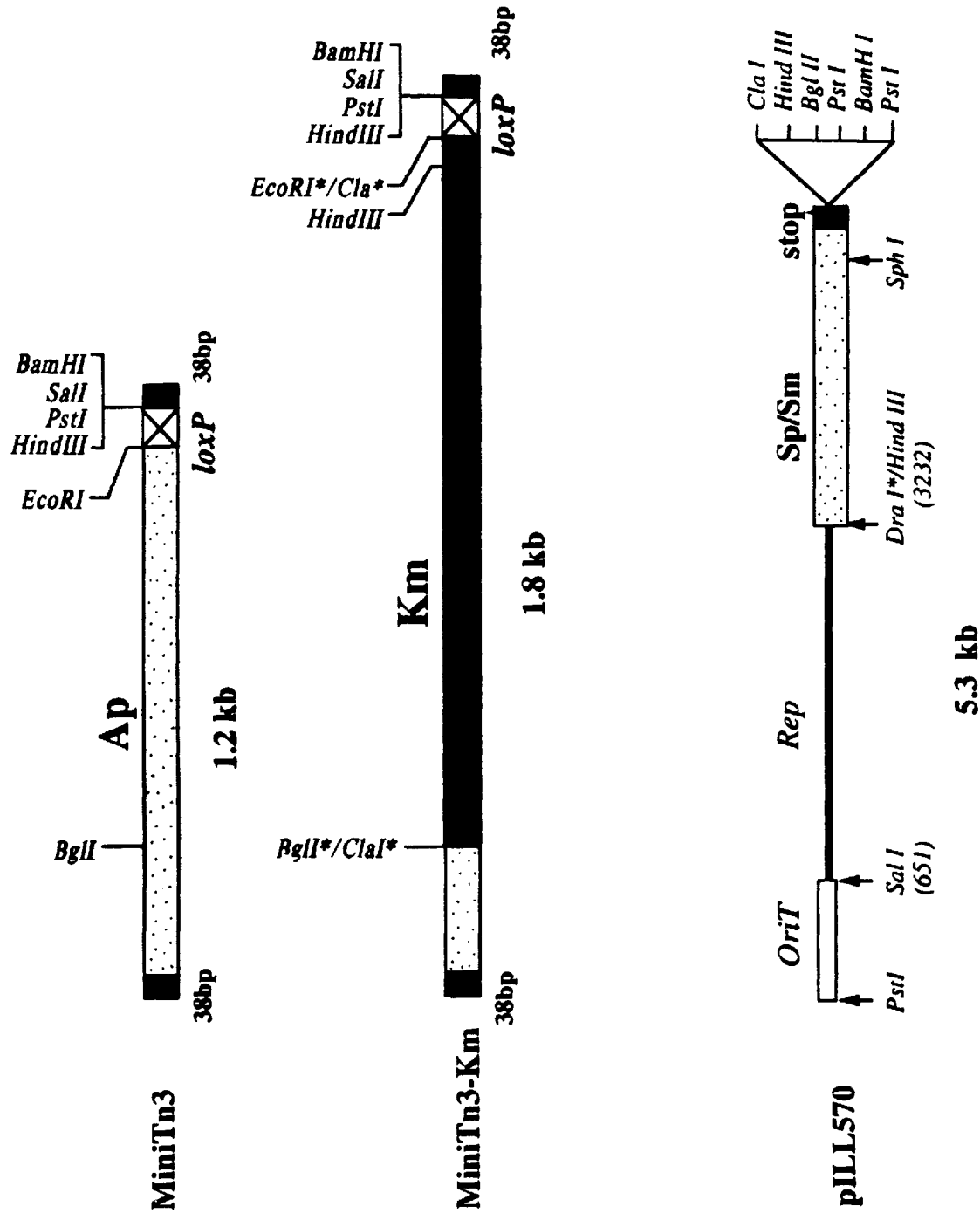

FIG. 13: Restriction map of MiniTn3 according to Seifert et al. (1986 PNAS, USA, 83: 735–739).

The asterisk indicates in the plasmid pILL570 the restriction sites which were modified during the construction of the vector.

I—IDENTIFICATION OF THE GENES

MATERIALS AND METHODS

Bacterial strains, plasmids and culture conditions

*H. pylori* 85P was isolated from a patient suffering from gastritis, and corresponds to the strain described in Labigne et al. (J. Bacteriol. 173: 1920–1931 (1991)). *E. coli* MC1061 (Maniatis et al. (1983), Molecular cloning: A laboratory manual. Cold Spring Harbor Laboratory, Cold Spring Harbor N.Y.) was used as host in the cloning experiment and *E. coli* HB101 (HsdR hsdM reA supE44 lacZ4 LeuB6 proA2 thi-1 SM) (Boyer et al. (1969) J. Mol. Biol. 41: 459–472) was used as host for the quantitative analysis of the expression of urease. The vectors and hybrids used in this study are shown in Table 1. The *E. coli* strains were grown in L broth without glucose (10 g of tryptone, 5 g of yeast extract and 5 g of NaCl per liter, pH=7.0) or on L gelose plates (containing 1.5% gelose) at 37° C. The antibiotic concentrations for the selection of the transformants were the following (in milligrams per liter): kanamycin: 20, tetracycline: 2, ampicillin: 100, spectinomycin: 100, carbenicillin: 100. For the expression of urease activity, the *E. coli* bacteria were grown on a medium limiting the concentration of the nitrogen source constituted of a gelose-containing minimal M9 medium without ammonium ions (pH=7.4) containing 0.4% D-glucose as carbon source and, unless otherwise indicated, 0.2% (wt/v) of L-glutamine sterilized by filtration and freshly prepared (Pahel et al. (1982) J. Bacteriol. 150: 202–213) as nitrogen source.

Molecular cloning and DNA analyses

The digestions with a restriction endonuclease, the filling of the ends and the other standard operations concerning DNA were performed according to the standard procedures of Maniatis et al. (Maniatis et al. (1983), Molecular cloning: A laboratory manual. Cold Spring Harbor Laboratory, Cold Spring Harbor N.Y.). The partial digestions with Sau3A were performed at 20° C. so as to retard enzymatic activity. The restriction endonucleases, the large fragment of DNA polymerase I, T4 DNA polymerase (used to create blunt fragment ends) and T4 DNA ligase were supplied by Amersham Corp. Calf intestinal alkaline phosphatase was supplied by Pharmacia. The DNA fragments were separated by electrophoresis on horizonal gel slabs containing 1 or 1.4% agarose and treated with Tris-acetate or Tris-phosphate buffers (Maniatis et al. (1983), Molecular cloning: A laboratory manual, Cold Spring Harbor Laboratory, Cold Spring Harbor N.Y.). A scale of 1 kb (Bethesda Research Laboratories) was used as molecular weight standard. Electroelution of the DNA fragments from the agarose gels containing ethidium bromide (0.4 μg/ml) was performed as previously described (J. Bacteriol. 173: 1920–1931 (1991), Labigne et al.).

Urease activity

Urease activity was detected by resuspension of $10^9$ bacteria in 1 ml of urea-indole medium (Diagnostic Pasteur) and incubation at 37° C. for variable times. The release of ammonia due to urease activity raised the pH causing a colour change from orange to red.

The urease activity was measured according to the Berthelot reaction according to a modification of the procedure previously described (Ferrero et al. (1991) Microb. Ecol. Hlth. Dis. 4: 121–134). Briefly, the bacteria were harvested from the gelose plates in 2.0 ml of sterile 0.85% NaCl and centrifuged at 12000 revs/min for 10 minutes at 4° C. The pellets were washed twice with 0.85% NaCl and resuspended in 100 mM sodium phosphate buffer (pH 7.4) containing 10 mM EDTA (PEB). In order to prepare sonicated extracts, the cells were lysed by four 30 s impulses from a Branson Sonifier Model 450 set at 30 W, 50% duty cycle. The cell debris were removed before the urease determinations were made. The freshly prepared samples (10–50 µl) were added to 200 µl of urea solution substrate (50 mM urea prepared in PEB) and allowed to react at room temperature for 30 minutes. The reactions were stopped by the addition of 400 µl of phenol-nitroprusside reagent and 400 µl of alkaline hypochlorite reagent. The reaction mixture was incubated at 50° C. Blanks in which urease activity was inactivated by boiling for 5 minutes before the addition of the substrate were treated similarly. The quantity of ammonia released was determined using a calibration curve establishing the relationship between $A_{625}$ and the ammonium ion concentration (from $NH_4Cl$). It was assumed that the release of 2 µmol of ammonia is equivalent to the hydrolysis of 1 µmol of urea. Urease activity was expressed in umol or urea hydrolysed/min/mg of bacterial protein.

Protein determinations

The protein concentrations were determined according to the Bradford assay (Sigma Chemicals). In order to solubilize the proteins in the whole cell extracts, the cell suspensions prepared in TPE were centrifuged and the pellets were resuspended in a solution of octyl-beta-D-glucopyranoside inorder to establish a final detergent concentration (in the staining reagent) of 0.1–0.2% (wt/V).

Transposon mutagenesis and construction of mutants

The MiniTn3-Km delivery system was used to produce mutations be random insertion in the DNA fragment cloned in pILL570.

The MiniTn3 system described by Seifert et al. (1986 PNAS USA 83: 735–739) making use of the plasmid pOX38 as donor of the transposable element and the trans-acting plasmid pTCA and supplying the enzyme transposase Tn3 (Seifert et al. 1985 Genetic Engineering Principles and Methods Vol. 8: p.123–134 Setlow, J. and Hollaeinder, A., Editors, Plenum Press New-York) and the strain NS2114 harbouring the cre gene coding for the recombinase P1 specific for the lox site were used for the mutagenesis of DNA fragments with the following modifications:

i) the MiniTn3 was modified by removing the BglI-EcoRI fragment of the gene coding for the beta-lactamase in the plasmid pTn (Seifert et al. 1986, already cited) and by replacing it with the ClaI—C. jejuni kanamycin cassette (1.4 kb long described by Labigne-Roussel et al (1988 J. Bacteriol. 170: 1704–1708)). This novel insertion agent MiniTn3-Km was transposed into the transferable plasmid pOX38 as described by Seifert et al. (1986 already mentioned) which leads to the production of the plasmid pILL553;

ii) the conjugative spectinomycin suicide vector pILL570 already described by Labigne et al. (1991 J. Bacteriol. 173: 1920–1931) was used for the cloning of the fragment used for mutagenesis. This suicide vector was derived from pILL560 (Labigne-Roussel et al. 1988 J. Bacteriol. 170: 1704–1708) whose DNA sequences responsible for immunity to Tn3 have been deleted;

iii) the plasmid IncP, pRK212.1 of the "complementing plasmid" (Figurski et al. 1979 PNAS USA 76: 1648–1652) was introduced by conjugation into the E. coli strain NS2114 and a spontaneous rifampicin mutant of NS2114 harbouring the cre gene was obtained and used for the selection of the transconjugants harbouring the cointegrate;

iv) the effective resolution of the cointegrates (products of cointegration) was positively selected owing to the large number of copies of the plasmid derived from pILL570 by depositing on plates the third mixture obtained on a medium containing 500 µg of kanamycin and 300 µg of spectinomycin.

DNA sequencing

Suitable DNA fragments were cloned in M13mp19 and M13mp18 (Messing et al. (1982) Gene 19: 269–276) in order to read the two complementary strands independently. The clones containing the insertion fragments were identified with the aid of X-Gal (5-bromo-4-chloro-3-indolyl-beta-D-galactopyranoside) and isopropyl-beta-D-thiogalactopyranoside. The single strands of the recombined plasmids M13mp18 and M13mp19 were obtained by the polyethylene glycol method (Sanger et al. (1980) J. Mol. Biol. 143: 161–178). The sequencing was performed according to the chain termination method using dideoxynucleotides (Sanger et al. (1977) Proc. Natl. Acad. Sci. USA 74: 5463–5467) with the aid of the necessary Sequenase (United States Biochemical Corp.). The sequencing of the double-stranded DNA was also carried out by the chain termination method using dideoxynucleotides with the necessary Sequenase by use of plasmid DNA purified on a cesium chloride gradient (Zhang et al. (1988) Nucleic Acids Research 16: 1220). Three microgram samples of DNA were first denatured with a 1 M NaOH solution (total volume 20 µl), then neutralized with 2 µl of 2M ammonium acetate (pH 4.6). The DNA was precipitated after addition of 60 µl of cold 100% ethanol, incubation at −70° C. for 10 minutes and centrifugation at 4° C. for 20 minutes. After washing with 60 µl cold 80% ethanol, the pellet was resuspended in 10 µl of sequencing buffer containing 0.5 pmol of primer and incubated for 3 minutes at 65° C. After incubation for 30 minutes at room temperature the sequencing was carried out.

RESULTS

Detection of urease activity in a E. coli host strain harbouring the recombinant cosmid pILL585

E. coli transformants harbouring the cosmid pILL585 were spread on glucose-containing minimal M9 medium supplemented with 0.2% of L-glutamine (as sole nitrogen source) or L medium and incubated at 37° C. for 48 hours. The transformants were then screened for urease activity by means of a quantitative colorimetric assay carried out in a urea-indole medium. The activity was only observed in the transformants of E. coli HB101 which had undergone several passages (more than 5 passages) on the minimal medium at 37° C. under aerobic conditions. These are thus the conditions which were used for the qualitative determination of the expression of urease in the E. coli clones. No urease activity was detected in the transformants grown on a medium rich in nitrogen.

The transformation of the E. coli strain HB101 with the plasmid pILL590 containing a fragment of 4.2 kb identified as the minimal region necessary for the expression of urease in C. jejuni (Labigne et at. (1991) J. Bacteriol. 173: 1920–1931) in E. coli cells even after culture and passage in a medium in which the concentration of nitrogen source is limiting. This implies that the genes present on the cosmid but absent from the plasmid pILL590 are necessary for the expression of urease in E. coli.

Subcloning of the genes necessary for the urease activity in an E. coli strain

In the absence of detectable urease activity in the E. coli strain harbouring the recombinant plasmid pILL590, the 34 kb insertion fragment of the cosmid pILL585 was subjected to partial digestion with the endonuclease Sau3A in order to produce fragments included between 7 and 12 kb. They were treated with alkaline phosphatase to prevent any rearrangement of the initial genome and ligated to the linearized plasmid pILL570 with BamHI. After transformation in *E. coli* HB101, each transformant resistant to spectinomycin was subjected to a subsequent assay of its capacity to hydrolyse urea under induction conditions. One clone exhibited a urease-positive phenotype. It harboured a recombinant plasmid called pILL753. This plasmid contained an insertion fragment of 11.2 kb. The recognition sites BamHI and HindIII were mapped relative to the unique EcoRI and PstI restriction sites of the vector pILL570 (FIG. 1). The comparison of the restriction map of the plasmid pILL753 with that of the recombinant plasmid previously described showed that the insertion fragment of pILL753 had an additional DNA fragment of 4.6 kb situated downstream from the four genes for urease previously identified in the plasmid pILL590 (i.e. ureA, ureB, ureC and ureD).

Optimization of urease activity in *E. coli* HB101

In order to define the growth conditions which ensure the optimal expression of the urease genes of *H. pylori* in *E. coli*, the activity of the clones harbouring pILL753 was assessed quantitatively after culture on minimal medium supplemented with various nitrogen sources. In all cases, a solid minimal basic medium was used since studies have shown that the urease activity was very low in cultures grown in a liquid medium.

The relative activities of the cultures on media supplemented with L-arginine, L-glutamine, L-glutamate, $NH_4Cl$ and urea (each at a final concentration of 10 mM) were, respectively: 100%, 36%, 27%, 46% and 20%.

The urease activity was optimal in the cultures grown on a medium supplemented with L-arginine. Urease activity was not detected in cultures grown on a medium rich in nitrogen.

Although the presence of free $Ni^{2+}$ ions may have a stimulatory effect on the urease activity (Mulrooney et al. (1989) J. Gen. Microbiol. 135: 1769–1776 and Mobley et al. (1989) Microbiol. Rev. 53: 85–108) this was not shown on the urease activity of the cells harbouring pILL753.

The analysis during the expression of urease in the *E. coli* clone carrying pILL753, grown under various conditions has shown that maximal urease activity was obtained after 3 days of aerobic culture at 37° C. on minimal medium supplemented with L-arginine (FIG. 2). The urease activity in the cultures grown on a medium rich in nitrogen was higher after culture in microaerobiosis. On the other hand, microaerobic conditions had a repressive effect on the activities of the nitrogen-limiting cultures.

The urease activity of the *E. coli* cells harbouring pILL753 in culture under aerobic conditions for 3 days at 37° C. in a minimal medium supplemented with arginine was 0.9+/–0.4 μmol or urea hydrolysed per minute per mg of protein. In comparison, the *H. pylori* isolate used for cloning the urease genes hydrolysed urea at a rate of 23.2+/–2.3 umol/mn/mg protein.

Identification and localisation of the genes necessary for urease activity in a *E. coli* host strain.

In order to define the DNA necessary for the urease-positive phenotype, derivatives of pILL753 carrying the transposable element MiniTn3-Km were first isolated according to a procedure previously described (see Materials and Methods). *E. coli* HB101 transformants carrying the transposons were all screened with regard to urease activity. They were called pILL753::x where x designates the insertion site of MiniTn3-Km as shown on the map in FIG. 1. Out of the 24 insertions selected for the analysis, 10 derivatives had totally lost the capacity to hydrolyse urea (2, 3, 4, 5, 6, 10, 11, 12, 13 and 14). whereas 14 conserved the urease-positive phenotype. These results confirm that every insertional mutation which maps in the ureA and ureB genes (mutants 2, 3, 4, 5 and 6) abolishes urase activity but show also that a DNA fragment of 2.6 kb situated further downstream from ureB is necessary for the expression of a urease-positive phenotype in *E. coli* grown under nitrogen-limiting conditions. On the other hand, from the results relating to transposon mutagenesis, a DNA fragment of 600 bp situated immediately downstream from the ureB gene has not been shown to be essential for the expression of urease activity in *E. coli*.

Additional analyses including the establishment of deletions in the insertion fragment pILL753 have been carried out in order to obtain a better understanding of the conditions necessary for the expression of an active urease in *E. coli* cells, *E. coli* subclones carrying the plasmid derivatives have been subjected to the quantitative determination of urease activity under the nitrogen-limiting conditions defined above. The results are summarized in Table 2. All of the subclones were derivatives of the same vector pILL570 so that the results can be compared. One of them, plasmid pILL768, was obtained by autoligation of the large EcoRI fragment produced from the digestion product using a restriction enzyme of the plasmid pILL753::16 (FIG. 1). This construction led to a deletion of 2.95 kb at the 3' end of the insertion segment pILL753. The cells carrying this plasmid express a comparatively low urease activity (Table 2). The plasmid pILL763 was obtained by cloning of the ClaI-PstI restriction fragment of the plasmid pILL753::1 in the linearised vector pILL570. This construction in which a DNA fragment of 1.75 kb containing the previously described genes ureC and ureD was deleted, expressed a urease activity approximately twice as high as those of the cells harbouring pILL753. In no case did deletions or insertions lead to constitutive urease activity.

Analysis of the sequence of the region necessary for the expression of urease in *E. coli*

In the 11.2 kb fragment necessary for the expression of urease in *E. coli*, a DNA fragment of 3.2 kb localized immediately downstream from the ureB gene was identified following the strategy of FIG. 3.

i) the 1.2 kb HindIII fragment and the 1.3 kb BamHI-HindIII fragment were sequenced independently after:
a) cloning of the previously mentioned restriction fragments, b) SpHI-BamHI, SpHI-HindIII fragments, c) BamHI-HindIII fragments of the plasmids pILL753::12, pILL753::11; pILL753::10 in the DNA of the phages M13mp18 and M13mp19;

ii) the 1.2 kb HindIII, 3.8 kb BamHI-PstI and 1.3 kb BamHI-PvuII restriction fragments derived from the plasmids pILL753 and pILL589 (previously described) were cloned in the DNA of the phages M13mp18 and M13mp19;

iii) twelve oligonucleotide primers were synthesized to confirm the reading and to produce sequences overlapping the three sequenced fragments independently. These primers were used for sequence analyses of double stranded DNA.

The sequence analysis revealed five open reading frames (ORFs) called ureI, ureF, ureG and ureH. These genes are all transcribed in the same direction and it is anticipated that they code for peptides of 195, 170, 256, 199 and 256 amino acids. An ORF of appreciable length was not observed on the reverse complement of the sequence illustrated in FIG. 4. The five ORFs commence with the characteristic starting codon ATG. Four of the five ORFs were preceded by sites similar to the *E. coli* consensus sequence for ribosome binding (Shine-Dalgarno) (Shine et al. (1974) Proc. Natl. Acad. Sci. USA 71: 1342–1346).

The regions upstream from each ORF have been the subject of research for the presence of nitrogen regulation sites with the sequence TGGYAYRN$_4$YYGCZ (SEQ ID NO:10) in which Y=T or C, R=G or A and Z=A or T (Morett et al. (1989) J. Mol. Biol. 210: 65–77). Only one site was found at 210 bp upstream from the ureG locus. Its precise position is shown in FIG. 4. Consensus sequences of the *E. coli* promoter type (σ70) were observed upstream from the genes ureI, ureF and ureH (TTGACA, −35 and TATAAT, −10 (SEQ ID NOS:11 and 12 respectively)).

nitrogen-limiting source. The results obtained have made it possible to show that the urease genes of *H. pylori* are probably under the control of the nitrogen regulatory system (NTR); and that the urease activity in the *E. coli* cells is dependent on the presence of a set of genes which have been described in the preceding pages. This set of genes has been localised immediately downstream from the four genes ureA, ureB, ureC and ureD described in the publication by Labigne et al., 1991, mentioned above. These novel genes are situated on a 3.2 kb fragment comprising five open reading frames which are designated ureI, ureE, ureF, ureG, and ureH.

TABLE 1

Hybrid vectors and plasmids used in the context of this study

| Plasmid | Vector | Phenotypic* characteristics | Size (kb) | Origin of the insertion | Références |
|---------|--------|-----------------------------|-----------|-------------------------|------------|
|         | pILL550 | RepEcRepCj mob Km | 8,3 |  | Labigne-Roussel et al |
|         | pILL570 | RepEcmob Sp | 5,3 |  | Labigne A. et al |
|         | pILL575 | RepEcRepCj mob Km Cos | 10 |  | Labigne A. et al |
| pILL585 | pILL575 | RepEcRepCj mob Km Cos | 44 | Sau3A partial digest of 85P | Labigne A. et al |
| PILL590 | pILL550 | RepEcRepCj mob Km | 16,4 | Sau3A partial gigest of PILL585 | Labigne A. et al |
| pILL753 | pILL570 | RepEcmob Sp | 16,5 | Sau3A partial digest of PILL585 | described here |
| pILL763 | pILL570 | RepEcmob Sp | 14,75 | Fragment Cla1-Pst1 of pILL753::1 | described here |
| pILL768 | pILL570 | RepEcmob Sp | 15,35 | Fragment EcoR1 of pILL753::16 | described here |

*RepEc and RepCj: plasmids capable of replicating in *E.coli* and *C.jejuni* respectively
mob: transposable plasmid due to presence of Ori-T
Km and Sp: resistance to kanin and spectinomycin
Cos: presence of a cos site

TABLE 2

Mutagenesis of the cloned DNA of *H. pylori* and effect on the urease activity in the *E. coli* HB101 clones grown under nitrogen-limiting conditions.

| Plasmid | *E.coli*HB101 pILL753 | (umol urea/min. mg). |
|---------|----------------------|----------------------|
| pILL753 (2) | — | 0,86 ± 0,39 |
| pILL753::3 | ureA degrad ed | neg (3) |
| pILL753::6 | ureB degraded | neg |
| pILL753::8 | ureI degraded | 1,1 ± 0,23 |
| pILL753::10 | ureF degraded | neg |
| pILL753::11 | ureG degraded | neg |
| pILL753::13 | ureH degrad | neg |
| pILL753::16 | insertion downstream from ureH | 0,66 ± 0,11(4) |
| pILL768 | deletion at 3' downstream from ureH | 0,57 ± 0,28 |

(1) Bacteria grown in aerobic medium for 3 days on M9 minimal medium medium supplemented with 0.01 M L-arginine at 37° C.
(2) For comparison, the urease activity of *H.pylori* 85P, the isolate from which the DNA was cloned, was 23 +/− 2.3 umol urea/min./mg protein.
(3) No urease activity was detected.
(4) Result of one particular measurement: 0.73
(5) Result of one particular measurement: 0.01

DISCUSSION

The first case of the functional expression in *E. coli* strains of genes derived from *H. pylori* is presented here.

This has been possible by growing *E. coli* cells harbouring the urease recombinant cosmid pILL585 (Labigne et al., mentioned above-1991) on a minimal medium containing a The use of insertional mutations and deletions in the 11.2 kb DNA fragment (pILL753) subcloned from the original cosmid has made it possible to show that the genes ureA, ureB, ureF, ureG and ureH are necessary for the expression of urease activity in *E. coli*. On the other hand, insertional mutations within the ureI gene do not appreciably affect urease activity in the *E. coli* cells. The deletion of the ureC gene and the ureD gene (as in the plasmid pILL763) resulted in activities which were significantly higher than those obtained in the cells carrying the plasmids with the loci intact, suggesting a regulatory role of this region of the urease gene cluster in *H. pylori*.

It seems clear that pILL753 probably does not carry the set of elements necessary for the complete expression of urease. The principal proof for that is that: on the one hand, the *E. coli* cells harbouring pILL753 had a urease activity approximately 25 times lower than that of the *H. pylori* isolate used initially for cloning; on the other hand, the deletion of the region downstream from ureH (pILL768) led to a considerable diminution of urease activity. It is interesting to note that *C. jejuni* requires the presence of a smaller number of genes for enzymatic expression compared with the results obtained in *E. coli*. Consequently, *C. jejuni* must be capable of complementing the functions of the cloned genes of *H. pylori*.

The requirement for accessory genes has also been demonstrated for *Providencia stuartii* (Mulrooney et al. (1988) J. Bacteriol. 170: 2202–2207), a urease-positive *E. coli* (Collins et al.-1988) *Klebsiella pneumonia* (Gerlach et al (1988) FEMS Microbiol. Lett. 50: 131–135), *Proteus vulgaris* (Mörsdorf et al. (1990) FEMS Microbiol. Lett. 66:

67–74), *Staphylococcus saphrophyticus* (Gatermann et al. (1989) Infect. Immun. 57: 2998–3002) *Klebsiella aerogenes* (Mulrooney et al.-1990) and *Proteus mirabilis* (Jones et al. (1989) J. Bact. 171: 6414–6422 and Walz et al. (1988) J. Bacteriol. 170: 1027–1033).

FIG. 5 presents a comparison of three regions coding for urease, in several species of bacteria and shows the similarities as well as the distinctive characteristics of each. The degree of relatedness in terms of genetic organization and polypeptides encoded is stronger between *P. mirabilis* and *K. aerogenes* than for each of the others in comparison with *H. pylori*. Whereas the polypeptide UreG of *H. pylori* exhibited a strong similarity with that of *K. aerogenes* (92% conserved and 59% identical), the degrees of conservation and identity between the polypeptides UreE and UreF of *H. pylori* and *K. aerogenes* were: (33% and 14%), (44% and 11.6%), respectively. Mulrooney et al. observed that the *K. aerogenes* genes coding for the accessory proteins UreE, UreI and UreG are implicated in the activation of the apoenzyme by incorporation of nickel into the urease subunits. Owing to the presence of series of histidine residues at the carboxyl terminus of the polypeptide UreE of Klebsiella and Proteus, Mulrooney et al. proposed that UreE might interact with the nickel in order to transfer it subsequently to the aopoenzyme. Such a series of residues has not been found in the polypeptide UreE of *H. pylori* nor in any other products of the urease genes.

The search for similarities between the amino acid sequence deduced from the urease genes of *H. pylori* and the consensus sequences implicated in a DNA binding site (Pabo et al.-1981) or in ATP binding sites (Higgins et al.-1985) has made possible the identification of a DNA binding site within the product of the ureI gene (FIG. 4). Furthermore, a well-conserved ATP binding site (-GVCGSGKT-) exists at the $NH_2$-terminus of the product of the ureG gene.

The urease region of *H. pylori* exhibits the following unique elements: first the genes ureC, ureD, ureI are unique for *H. pylori*. Then the urease region consists of three blocks of genes which are transcribed in the same direction and possess and intergenic region of 420 bp between ureD and ureA and 200 bp between ureB and ureI. This suggests a genetic organization peculiar to *H. pylori*, in which the three blocks of genes can be regulated independently.

It is generally accepted that the synthesis of urease by *H. pylori* is constitutive. The results presented here tend to show that the expression of the urease genes of *H. pylori* might in fact be under the control of a regulatory system. In fact, the expression of the urease genes of *H. pylori* once transferred to *E. coli* is completely under the control of the nitrogen regulatory system (NTR). It is possible that the urease genes of *H. pylori* are directly dependent on the synthesis of the products of the ntrA, ntrB, ntrC genes of *E. coli* but it can not be excluded that they are dependent on the expression of one or more other genes coding for one or more regulatory protein(s) similar to the ntr products of *E. coli*. On the basis of these data it may be imagined that physiological parameters such as the presence of a solid medium or a microaerophilic atmosphere may play a role in the expression or urease in *H. pylori* in vitro or in vivo.

II—PREPARATION OF MUTANT STRAINS

Strains used for the electroporation experiments: several strains isolated from biopsies were tested for their capacity to be electroporated, including the strain 85P described in the publication by Labigne et al.-1991, mentioned above, from which the initial cloning of the urease genes was accomplished. A single strain designated N6 deposited with the CNCM under the number I-1150 on Oct. 3, 1991 gave positive results.

Creation of mutants in the cloned fragment of the chromosome of *H. pylori*, strain 85P: the mutants are prepared by mutagenesis by means of a transposon (MiniTn3-Km) which enables the element (transposition element) to be inserted randomly. The insertion site of each of the transposition elements was defined by restriction analysis of the derived plasmids (cf. FIG. 1).

Electroporation: $10^{10}$ cells of *H. pylori* were harvested on blood gelose (10% horse blood) washed with glycerol/sucrose solution (15% v/v and 9% wt/v) and resuspended in a volume of 50 µl at 4° C. 500 ng of plasmid DNA purified on CsCl and dialysed immediately against distilled water were added in a volume of 1 µl to the cells at 4° C. After 1 minute on ice the cells and the DNA were transferred to an electroporation cuvette precooled to −20° C. (BioRad catalogue No: 165–2086, 0.2 cm wide), then placed in the Gene pulser apparatus-BioRad which was set at the following parameters :25 F, 2.5 kV and 200 ohms. After delivery of the electrical impulse with constant times of 4.5 to 5 msec, the bacteria were resuspended in 100 µl of SOC buffer (2% Bacto tryptone, 0.5% Bacto yeast extract, 10 mM NaCl, 2.5 mM KCl, 10 mM $MgCl_2$, 10 mM $MgSO_4$, 20 mM glucose), and inoculated on nonselective blood gelose (without kanamycin, but including vancomycin, trimethoprim, polymixin, nalidixic acid, amphotericin B) for 48 hours at 37° C. under a microaerophilic atmosphere. The bacteria are then harvested, resuspended in a volume of Brucella medium (0.5 ml) and 100 µl of the suspension are spread on selective blood gelose plates (included 20 µg/ml of kanamycin and the antibiotic cocktail described above). The growth of the transformed bacteria resistant to kanamycin appears after 4 days' incubation at 37° C. in a microaerophilic atmosphere.

The other techniques including PCR and Southern and Western blots are standard procedures.

RESULTS

Two mutations generated by insertion of MiniTn3-Km into the ureB gene present in the plasmid pILL753 were studied in detail. They are the mutations numbered 3 and 4. The precise position of each of the insertions is given in FIG. 6. The plasmids corresponding to these insertions were prepared, purified and concentrated. Bacteria resistant to kanamycin exhibiting all of the characteristics of strain N6 or *H. pylori* used for electroporation were obtained; they are completely incapable of hydrolysing urea.

Controls have made it possible to verify that the mutant strain is an isogenic strain:

although "urease negative" the strains have the characteristic biochemical properties of the bacteria belonging to the species *H. pylori* (oxidase, catalase, sensitivity to oxygen);

the parent bacteria (N6) (CNCM No. I-1150) and the isogenic bacteria N6::TnKm-3 and N6:TnKm-4 have the same restriction profiles after enzymatic digestion of the total DNAs (cf. FIG. 8);

after enzymatic amplification with the aid of primers specific for *H. pylori* and sequencing of the amplified product the same nucleotide sequences were found whereas independent strains of *H. pylori* never exhibit the same sequence but, rather, considerable genetic polymorphism:

analysis by Southern type hybridization of the restriction profiles resulting from BamHI and HindIII of the DNA of the parental and mutant strains provides evidence of the replacement of the genes (FIG. 7 and its interpretation FIG. 6).

One of the difficulties encountered results from the fact that the transformed strain (N6) is not the one from which the cloning of the urease genes was performed, this latter strain being the strain 85P and that the HindIII and BamHI restriction sites are not conserved from one strain to another: a probe corresponding to the 8.1 kb fragment derived from pILL590 (FIG. 1) clearly shows HindIII restriction profiles which differ between N6 and 85P (FIG. 9), in particular the absence of 1.25 kb and 1.15 kb fragments. On the other hand, the HindIII 4.1 kb fragment and the BamHI 5.1 kb and 1.3 kb fragments are conserved. Hence it has been confirmed by enzymatic amplification (PCR) with the aid of oligonucleotides distributed over the entire region corresponding to the genes ureA, ureB, ureC and ureD that the amplification products 1 to 6 shown in FIG. 10 are the same in both strains, and that the absence of the HindIII restriction sites reflects gene polymorphism and not a major rearrangement of the urease region. Such confirmation makes it possible to confirm unambiguously the gene replacement of the wild-type allele by the mutant allele in the two mutants created.

finally, it was confirmed by immunoblotting with the aid of anti-urease or anti-*H. pylori* antibodies prepared in the rabbit, or anti-*H. pylori* present in the serum of patients infected by *H. pylori* that the mutant strains N6::TnKm-3 and N6::TnKm4 no longer express the 61 KDaltons polypeptide encoded in the ureB gene and hence that the ureB gene of these strains has indeed been interrupted (FIG. 11).

We claim:

1. A purified nucleic acid sequence comprising at least one gene selected from the group consisting of ureE, ureF, ureG, ureH, and UreI represented by nucleotides 800 to 1309, 1324 to 2091, 2123 to 2719, 2722 to 3516, and 211 to 795, respectively, of SEQ ID NO:1 and FIG. 4.

2. A purified nucleic acid sequence comprising the ureE gene represented by nucleotides 800 to 1309 of SEQ ID NO:1 and FIG. 4 or a sequence comprising at least 20 contiguous nucleic acid residues that hybridizes under stringent conditions selected from the group consisting of:

a) 68° C. in 6×SSC Denhardt medium, and
b) 37° C. in 5×SSC 50% formamide, with the ureE sequence or with a sequence that is complementary to the ureE sequence and not to other sequences in *H. pylori*.

3. A purified nucleic acid sequence comprising the ureF gene represented by nucleotides 1324 to 2091 of SEQ ID NO:1 and FIG. 4 or a sequence comprising at least 20 contiguous nucleic acid residues that hybridizes under stringent conditions selected from the group consisting of:

a) 68° C. in 6×SSC Denhardt medium, and
b) 37° C. in 5×SSC 50% formamide, with the ureF sequence or with a sequence that is complementary to the ureF sequence and not to other sequences in *H. pylori*.

4. A purified nucleic acid sequence comprising the ureG gene represented by nucleotides 2123 to 2719 of SEQ ID NO:1 and FIG. 4 or a sequence comprising at least 20 contiguous nucleic acid residues that hybridizes under stringent conditions selected from the group consisting of:

a) 68° C. in 6×SSC Denhardt medium, and
b) 37° C. in 5×SSC 50% formamide, with the ureG sequence or with a sequence that is complementary to the ureG sequence and not to other sequences in *H. pylori*.

5. A purified nucleic acid sequence comprising the ureH gene represented by nucleotides 2722 to 3516 of SEQ ID NO:1 and FIG. 4 or a sequence comprising at least 20 contiguous nucleic acid residues that hybridizes under stringent conditions selected from the group consisting of:

a) 68° C. in 6×SSC Denhardt medium, and
b) 37° C. in 5×SSC 50% formamide, with the ureH sequence or with a sequence that is complementary to the ureH sequence and not to other sequences in *H. pylori*.

6. A purified nucleic acid sequence comprising the ureI gene represented by nucleotides 211 to 795 of SEQ ID NO:1 and FIG. 4 or a sequence comprising at least 20 contiguous nucleic acid residues that hybridizes under stringent conditions selected from the group consisting of:

a) 68° C. in 6×SSC Denhardt medium, and
b) 37° C. in 5×SSC 50% formamide, with the ureI sequence or with a sequence that is complementary to the ureI sequence and not to other sequences in *H. pylori*.

7. A purified nucleic acid sequence according to any one of claims 2–6, wherein the hybridizing sequence encodes a polypeptide that functions with *H. pylori* as a polypeptide encoded by the gene from which the nucleic acid sequence was derived.

8. A purified nucleic acid sequence according to any one of claims 2–6, wherein the hybridizing sequence encodes a polypeptide that is recognized by antibodies directed against *H. pylori* or behaves as a hapten or immunogen.

9. A purified nucleic acid sequence comprising a nucleic acid sequence according to any one of claims 2–6 and a nucleic sequence encoding UreA and UreB polypeptides of *H. pylori*.

10. A purified nucleic acid sequence comprising a nucleic acid sequence according to any one of claims 2–6 and a nucleic acid sequence selected from the group consisting of *H. pylori* genes ureA, ureB, ureC, and ureD.

11. A probe for the detection of a gene selected from the group consisting of ureE, ureF, ureG, ureH, and ureI of *H. pylori*, represented by nucleotides 800 to 1309, 1324 to 2091, 2123 to 2719, 2722 to 3516 and 211 to 795, respectively, of SEQ ID NO:1 and FIG. 4, or a complementary nucleotide sequence of said gene, wherein said probe hybridizes to said gene under stringent conditions and not to other sequences in *H. pylori*.

12. The probe of claim 11, wherein said gene is ureE, represented by nucleotides 800 to 1309 of SEQ ID NO:1 and FIG. 4.

13. The probe of claim 11, wherein said gene is ureF represented by nucleotides 1324 to 2091 of SEQ ID NO:1 and FIG. 4.

14. The probe of claim 11, wherein said gene is ureG represented by nucleotides 2123 to 2719 of SEQ ID NO:1 and FIG. 4.

15. The probe of claim 11, wherein said gene is ureH represented by nucleotides 2722 to 3516 of SEQ ID NO:1 and FIG. 4.

16. The probe of claim 11, wherein said gene is ureI represented by nucleotides 211 to 795 of SEQ ID NO:1 and FIG. 4.

17. A primer comprising from 18–30 nucleotides that hybridizes under stringent conditions or conditions suitable for gene amplification to a gene selected from the group consisting of ureE, ureF, ureG, ureH, and ureI of *H. pylori*, represented by nucleotides 800 to 1309, 1324 to 2091, 2123 to 2719, 2722 to 3516, and 211 to 795, respectively, of SEQ ID NO:1 and FIG. 4, or a complementary nucleotide sequence of said gene that specifically amplifies said gene and not other sequences in *H. pylori*.

18. A purified nucleotide sequence comprising the sequence (SEQ ID NO:8):

GCG AAA ATA TGC TAT GAA ATA GGA AAC CGC CAT.

19. The purified nucleotide sequence of claim 18, wherein said nucleotide sequence is labeled.

20. A method for the in vitro detection of *H. pylori* in a sample, said method comprising:

a) obtaining a biological sample comprising nucleic acid;
b) extracting nucleic acid from said biological sample and treating said nucleic acid with a reverse transcriptase to produce a double-stranded nucleic acid comprising said nucleic acid and its complementary strand;

c) a cycle comprising the following steps:

denaturing the double-stranded nucleic acid to be detected, forming single-stranded nucleic acids, hybridizing each of said single-stranded nucleic acids with at least one primer according to claim 17 by placing said single strand in contact with said primer under hybridization conditions, amplifying said single-stranded nucleic acids by elongation of said primer along the strands to which they are hybridized; and d) detecting the presence of amplified nucleic acid, wherein said detection is correlated with the presence or absence of *H. pylori.*

21. A method for the in vitro detection of an infection of *H. pylori* in a biological sample comprising placing the probe of claim 11 in contact with nucleic acids of said biological sample under hybridization conditions, and detecting a hybrid formed between the nucleic acid of *H. pylori* in the sample and said probe, wherein said detection is correlated with the presence or absence of an infection by *H. pylori.*

22. A method for the in vitro detection of an infection by *H. pylori* in a biological sample comprising placing the nucleotide sequence of claim 19 in contact with nucleic acids of said biological sample under hybridization conditions, and detecting a hybrid formed between the nucleic acid of *H. pylori* in the sample and said probe, wherein said detection is correlated with the presence or absence of an infection by *H. pylori.*

23. Recombinant vector comprising a nucleotide sequence according to any one of claims 1–6.

24. Recombinant vector according to claim 23, wherein said vector is a cosmid or plasmid.

25. Recombinant vector comprising the nucleotide sequence of claim 18.

26. Recombinant vector according to claim 25, wherein said vector is a cosmid or plasmid.

27. Recombinant vector according to claim 23, wherein said vector is the plasmid pILL753 contained in *E. coli* HB101 deposited with the CNCM or Oct. 3, 1991 under the number I-1148.

28. Recombinant vector according to claim 23, wherein said vector is the plasmid pILL763 contained in *E. coli* HB101 deposited with the CNCM or Oct. 3, 1991 under the number I-1149.

29. Recombinant cell host comprising a nucleotide sequence according to any one of claims 1–6, wherein said nucleotide sequence is expressed in said host.

30. The recombinant cell host of claim 29, wherein said host is *H. pylori.*

31. The recombinant cell host of claim 29, wherein said host is not *H. pylori.*

32. The recombinant cell host of claim 29, where said host is *E. coli.*

33. Recombinant cell host comprising a nucleotide sequence of claim 18, wherein said sequence is expressed in said host.

34. The recombinant cell host of claim 33, wherein said host is *H. pylori.*

35. The recombinant cell host of claim 33, wherein said host is not *H. pylori.*

36. The recombinant cell host of claim 33, wherein said host is *E. coli.*

37. A diagnostic kit for the in vitro diagnosis of an infection by *H. pylori* by detecting the presence of *H. pylori* nucleic acid or a strand of DNA complementary to said nucleic acid, said kit comprising at least one primer according to claim 17, wherein said primer hybridizes with *H. pylori* nucleic acid, and reagents for amplifying said nucleic acid.

38. A kit for the in vitro diagnosis of an infection by *H. pylori* comprising the probe of claim 11 and a medium suitable for carrying out a hybridization reaction between the nucleic acid of *H. pylori* to be detected and the probe.

39. A kit for the in vitro diagnosis of an infection by *H. pylori* comprising the nucleotide sequence of claim 19, and a medium suitable for carrying out a hybridization reaction between the nucleic acid of *H. pylori* to be detected and the nucleotide sequence.

40. A probe according to any one of claims 11–16, wherein said probe is labeled.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 3559 base pairs
      (B) TYPE: nucleic acid
      (C) STRANDEDNESS: unknown
      (D) TOPOLOGY: unknown (ii) MOLECULE TYPE: DNA (genomic)

(ix) FEATURE:
      (A) NAME/KEY: CDS
      (B) LOCATION: 2..16

(ix) FEATURE:
      (A) NAME/KEY: CDS
      (B) LOCATION: 211..795

(ix) FEATURE:
      (A) NAME/KEY: CDS
      (B) LOCATION: 800..1309

(ix) FEATURE:
      (A) NAME/KEY: CDS
      (B) LOCATION: 1324..2091

(ix) FEATURE:
      (A) NAME/KEY: CDS
      (B) LOCATION: 2122..2718

(ix) FEATURE:
      (A) NAME/KEY: CDS
      (B) LOCATION: 2721..3515

(xi) SEQUENCE DESCRIPTION: SEQ ID NO:1:

```
A CTC TTT AGC ATT TTC TAGGATTTTT TAGGAGCAAC GCTCTTAGAT CCTTAGTTTT        56
  Leu Phe Ser Ile Phe
   1               5

TAGCTCTCTG ATTTTTTGTT TATCAAAAAA TTGGGGGCTT TTTTTGTTTT TATTTTTTGT       116

CAATTTACTA TTTTTCTTTA TGATTAGCTC AAGCAACAAA AGTTATTCGT AAGGTGCGTT       176

TGTTGTAAAA ATTTTTGTTT GGAAGGAAAA GGCA ATG CTA GGA CTT GTA TTG           228
                                      Met Leu Gly Leu Val Leu
                                       1               5

TTA TAT GTT GGG ATT GTT TTA ATC AGC AAT GGG ATT TGC GGG TTA ACC     276
    Leu Tyr Val Gly Ile Val Leu Ile Ser Asn Gly Ile Cys Gly Leu Thr
```

```
                 10                  15                  20
AAA GTC GAT CCT AAA AGC ACT GCG GTG ATG AAC TTT TTT GTG GGT GGG       324
Lys Val Asp Pro Lys Ser Thr Ala Val Met Asn Phe Phe Val Gly Gly
         25                  30                  35

CTC TCC ATT ATT TGT AAT GTG GTT GTC ATC ACT TAT TCC GCT CTC AAC       372
Leu Ser Ile Ile Cys Asn Val Val Val Ile Thr Tyr Ser Ala Leu Asn
         40                  45                  50

CCT ACA GCC CCT GTA GAA GGT GCT GAA GAT ATT GCT CAA GTA TCA CAC       420
Pro Thr Ala Pro Val Glu Gly Ala Glu Asp Ile Ala Gln Val Ser His
55               60                  65                  70

CAT TTG ACT AAT TTC TAT GGG CCA GCG ACT GGG TTA TTG TTT GGT TTC       468
His Leu Thr Asn Phe Tyr Gly Pro Ala Thr Gly Leu Leu Phe Gly Phe
             75                  80                  85

ACC TAC TTG TAT GCG GCT ATC AAC CAC ACT TTT GGT TTG GAT TGG AGG       516
Thr Tyr Leu Tyr Ala Ala Ile Asn His Thr Phe Gly Leu Asp Trp Arg
         90                  95                  100

CCC TAC TCT TGG TAT AGC TTA TTC GTA GCG ATC AAC ACG ATT CCT GCT       564
Pro Tyr Ser Trp Tyr Ser Leu Phe Val Ala Ile Asn Thr Ile Pro Ala
         105                 110                 115

GCG ATT TTA TCC CAC TAT AGC GAT ATG CTT GAT GAC CAC AAA GTG TTA       612
Ala Ile Leu Ser His Tyr Ser Asp Met Leu Asp Asp His Lys Val Leu
120                 125                 130

GGC ATC ACT GAA GGC GAT TGG TGG GCG ATC ATT TGG TTG GCT TGG GGT       660
Gly Ile Thr Glu Gly Asp Trp Trp Ala Ile Ile Trp Leu Ala Trp Gly
135                 140                 145                 150

GTT TTG TGG CTT ACC GCT TTC ATT GAA AAC ATC TTG AAA ATC CCT TTA       708
Val Leu Trp Leu Thr Ala Phe Ile Glu Asn Ile Leu Lys Ile Pro Leu
             155                 160                 165

GGG AAA TTC ACT CCA TGG CTT GCT ATC ATT GAG GGC ATT TTA ACC GCT       756
Gly Lys Phe Thr Pro Trp Leu Ala Ile Ile Glu Gly Ile Leu Thr Ala
             170                 175                 180

TGG ATC CCT GCT TGG TTA CTC TTT ATC CAA CAC TGG GTG TGAG ATG ATC     805
Trp Ile Pro Ala Trp Leu Leu Phe Ile Gln His Trp Val     Met Ile
             185                 190                 195          1

ATA GAG CGT TTA ATA GGC AAT CTA AGG GAT TTA AAC CCC TTG GAT TTC       853
Ile Glu Arg Leu Ile Gly Asn Leu Arg Asp Leu Asn Pro Leu Asp Phe
         5                   10                  15

AGC GTG GAT TAT GTG GAT TTG GAA TGG TTT GAA ACG AGG AAA AAA ATC       901
Ser Val Asp Tyr Val Asp Leu Glu Trp Phe Glu Thr Arg Lys Lys Ile
         20                  25                  30

GCT CGC TTT AAA ACC AGG CAA GGC AAA GAC ATA GCC GTA CGC CTT AAA       949
Ala Arg Phe Lys Thr Arg Gln Gly Lys Asp Ile Ala Val Arg Leu Lys
35               40                  45                  50

GAC GCT CCC AAG TTG GGT TTC TCT CAA GGA GAT ATT TTA TTT AAA GAA       997
Asp Ala Pro Lys Leu Gly Phe Ser Gln Gly Asp Ile Leu Phe Lys Glu
             55                  60                  65

GAG AAG GAA ATT ATC GCC GTT AAT ATC TTG GAT TCT GAA GTC ATT CAC       1045
Glu Lys Glu Ile Ile Ala Val Asn Ile Leu Asp Ser Glu Val Ile His
         70                  75                  80

ATC CAA GCT AAG AGC GTG GCA GAA GTA GCG AAA ATA TGC TAT GAA ATA       1093
Ile Gln Ala Lys Ser Val Ala Glu Val Ala Lys Ile Cys Tyr Glu Ile
             85                  90                  95

GGA AAC CGC CAT GCG GCT TTA TAC TAT GGC GAG TCT CAA TTT GAA TTT       1141
Gly Asn Arg His Ala Ala Leu Tyr Tyr Gly Glu Ser Gln Phe Glu Phe
         100                 105                 110

AAA ACA CCA TTT GAA AAG CCC ACG CTA GCG TTA CTA GAA AAG CTA GGG       1189
Lys Thr Pro Phe Glu Lys Pro Thr Leu Ala Leu Leu Glu Lys Leu Gly
115                 120                 125                 130

GTT CAA AAT CGT GTT TTA AGT TCA AAA TTG GAT TCC AAA GAA CGC TTA       1237
Val Gln Asn Arg Val Leu Ser Ser Lys Leu Asp Ser Lys Glu Arg Leu
```

|  |  |  |  |  |  |  |  |  |  |  |  |  |  |  |  |
|---|---|---|---|---|---|---|---|---|---|---|---|---|---|---|---|
|  |  |  | 135 |  |  |  | 140 |  |  |  | 145 |  |  |  |  |

```
              135                  140                   145
ACC GTG AGC ATG CCC CAT AGT GAG CCT AAT TTT AAG GTC TCA CTG GCG      1285
Thr Val Ser Met Pro His Ser Glu Pro Asn Phe Lys Val Ser Leu Ala
                150                 155                 160

AGC GAT TTT AAA GTG GTC ATG AAA TAGAAAAACA ACAA ATG GAT AAA GGA      1335
Ser Asp Phe Lys Val Val Met Lys               Met Asp Lys Gly
            165             170                    1

AAA AGC GTG AAA AGC ATT GAA AAA AGC GTG GGT ATG CTC CCA AAA ACT      1383
Lys Ser Val Lys Ser Ile Glu Lys Ser Val Gly Met Leu Pro Lys Thr
  5               10                  15                  20

CCA AAG ACA GAC AGC AAT GCT CAT GTG GAT AAT GAA TTT CTG ATT CTG      1431
Pro Lys Thr Asp Ser Asn Ala His Val Asp Asn Glu Phe Leu Ile Leu
            25                  30                  35

CAA GTC AAT GAT GCG GTG TTC CCC ATT GGA TCT TAC ACG CAT TCT TTT      1479
Gln Val Asn Asp Ala Val Phe Pro Ile Gly Ser Tyr Thr His Ser Phe
        40                  45                  50

GGG CTT TTG GCT AGA AAC TTA CAT CCA GCA AAA AAG GTT ACT AAT AAA      1527
Gly Leu Leu Ala Arg Asn Leu His Pro Ala Lys Lys Val Thr Asn Lys
            55                  60                  65

GAA AGC GCT TTA AAA TAT TTA AAA GCC AAT CTC TCT AGC CAG TTC CTT      1575
Glu Ser Ala Leu Lys Tyr Leu Lys Ala Asn Leu Ser Ser Gln Phe Leu
 70                  75                  80

TAC ACG GAA ATG CTG AGC TTG AAA CTC ACC TAT GAA AGC GCT CTC CAA      1623
Tyr Thr Glu Met Leu Ser Leu Lys Leu Thr Tyr Glu Ser Ala Leu Gln
 85                  90                  95                 100

CAA GAT TTA AAA AGG ATC TTA GGG GTT GAA GAA ATC ATT ACG CTA TCC      1671
Gln Asp Leu Lys Arg Ile Leu Gly Val Glu Glu Ile Ile Thr Leu Ser
                105                 110                 115

ACA AGC CCC ATG GAA TTG CGA TTA GCC AAT CAA AAG CTA GGC AAT CGT      1719
Thr Ser Pro Met Glu Leu Arg Leu Ala Asn Gln Lys Leu Gly Asn Arg
            120                 125                 130

TTC ATT AAA ACC TTA CAA GCC ATG AAC GAA TTA GAC ATT GGC GCA TTT      1767
Phe Ile Lys Thr Leu Gln Ala Met Asn Glu Leu Asp Ile Gly Ala Phe
            135                 140                 145

TTT AAC GCT TAC GCT CAA CAA ACC GAA GAC CCC ACC CAT GCC ACT AGC      1815
Phe Asn Ala Tyr Ala Gln Gln Thr Glu Asp Pro Thr His Ala Thr Ser
        150                 155                 160

TAT GGC GTT TTT GCG GCG AGT TTG GGG ATT GAA TTG AAA AAG GCT TTA      1863
Tyr Gly Val Phe Ala Ala Ser Leu Gly Ile Glu Leu Lys Lys Ala Leu
165                 170                 175                 180

AGG CAT TAT CTT TAT GCA CAA ACT TCT AAC ATG GTA ATT AAC TGC GTT      1911
Arg His Tyr Leu Tyr Ala Gln Thr Ser Asn Met Val Ile Asn Cys Val
                185                 190                 195

AAA AGC GTC CCA CTA TCT CAA AAC GAT GGG CAA AAA ATC TTA TTG AGC      1959
Lys Ser Val Pro Leu Ser Gln Asn Asp Gly Gln Lys Ile Leu Leu Ser
            200                 205                 210

TTG CAA AGC CCT TTT AAC CAG CTC ATA GAA AAA ACC TTA GAA CTA GAC      2007
Leu Gln Ser Pro Phe Asn Gln Leu Ile Glu Lys Thr Leu Glu Leu Asp
        215                 220                 225

GAA AGC CAC TTG TGC GCG GCA AGC GTT CAA AAC GAC ATT AAG GCG ATG      2055
Glu Ser His Leu Cys Ala Ala Ser Val Gln Asn Asp Ile Lys Ala Met
            230                 235                 240

CAG CAT GAG AGT TTA TAC TCG CGC CTT TAT ATG TCT TGAATTTTAT           2101
Gln His Glu Ser Leu Tyr Ser Arg Leu Tyr Met Ser
245                 250                 255

CTCAAATTGA AAGGAATTTT ATG GTA AAA ATT GGA GTT TGT GGT CCT GTA        2151
                      Met Val Lys Ile Gly Val Cys Gly Pro Val
                        1               5                  10

GGA AGC GGT AAA ACC GCC TTG ATT GAA GCT TTA ACG CGC CAC ATG TCA      2199
Gly Ser Gly Lys Thr Ala Leu Ile Glu Ala Leu Thr Arg His Met Ser
```

```
              15                  20                  25

AAA GAT TAT GAC ATG GCG GTC ATC ACT AAT GAT ATT TAC ACG AAA GAA    2247
Lys Asp Tyr Asp Met Ala Val Ile Thr Asn Asp Ile Tyr Thr Lys Glu
            30                  35                  40

GAC GCA GAA TTT ATG TGT AAA AAT TCG GTG ATG CCA CGA GAG AGG ATC    2295
Asp Ala Glu Phe Met Cys Lys Asn Ser Val Met Pro Arg Glu Arg Ile
            45                  50                  55

ATT GGC GTA GAA ACA GGA GGC TGT CCG CAC ACG GCT ATT AGA GAA GAC    2343
Ile Gly Val Glu Thr Gly Gly Cys Pro His Thr Ala Ile Arg Glu Asp
            60                  65                  70

GCT TCT ATG AAT TTA GAA GCC GTA GAA GAA ATG CAT GGC CGT TTC CCT    2391
Ala Ser Met Asn Leu Glu Ala Val Glu Glu Met His Gly Arg Phe Pro
75                  80                  85                  90

AAT TTG GAA TTG CTT TTG ATT GAA AGC GGA GGC AGT AAC CTT TCA GCG    2439
Asn Leu Glu Leu Leu Leu Ile Glu Ser Gly Gly Ser Asn Leu Ser Ala
                95                 100                 105

ACT TTC AAC CCA GAG CTA GCG GAC TTT ACG ATC TTT GTG ATT GAT GTG    2487
Thr Phe Asn Pro Glu Leu Ala Asp Phe Thr Ile Phe Val Ile Asp Val
                110                 115                 120

GCT GAG GGC GAT AAA ATC CCC AGA AAA GGC GGG CCA GGA ATC ACG CGT    2535
Ala Glu Gly Asp Lys Ile Pro Arg Lys Gly Gly Pro Gly Ile Thr Arg
            125                 130                 135

TCA GAC TTG CTT GTC ATC AAT AAG ATT GAT TTA GCC CCC TAT GTG GGA    2583
Ser Asp Leu Leu Val Ile Asn Lys Ile Asp Leu Ala Pro Tyr Val Gly
140                 145                 150

GCC GAC TTG AAA GTC ATG GAA AGG GAT TCT AAA AAA ATC GCG GCG AAA    2631
Ala Asp Leu Lys Val Met Glu Arg Asp Ser Lys Lys Ile Ala Ala Lys
155                 160                 165                 170

AGC CCT TTA TTT TTA CCG AAT ATC CGC GCT AAA GAA GGT TTA GAC GAT    2679
Ser Pro Leu Phe Leu Pro Asn Ile Arg Ala Lys Glu Gly Leu Asp Asp
                175                 180                 185

GTG ATC GCT TGG ATC AAG CGC AAC GCT TTA TTG GAA GAT TG  ATG AAC    2726
Val Ile Ala Trp Ile Lys Arg Asn Ala Leu Leu Glu Asp     Met Asn
            190                 195                         1

ACT TAC GCT CAA GAA TCC AAG CTC AGG TTA AAA ACC AAA ATA GGG GCT    2774
Thr Tyr Ala Gln Glu Ser Lys Leu Arg Leu Lys Thr Lys Ile Gly Ala
        5                   10                  15

GAC GGG CGG TGC GTG ATT GAA GAC AAT TTT TTC ACG CCC CCC TTT AAG    2822
Asp Gly Arg Cys Val Ile Glu Asp Asn Phe Phe Thr Pro Pro Phe Lys
        20                  25                  30

CTC ATG GCG CCC TTT TAC CCT AAA GAC GAT TTA GCG GAA ATC ATG CTT    2870
Leu Met Ala Pro Phe Tyr Pro Lys Asp Asp Leu Ala Glu Ile Met Leu
35                  40                  45                  50

TTA GCG GTA AGC CCT GGC TTA ATG AAA GGC GAT GCA CAA GAT GTG CAA    2918
Leu Ala Val Ser Pro Gly Leu Met Lys Gly Asp Ala Gln Asp Val Gln
                55                  60                  65

TTG AAC ATC GGT CCA AAT TGC AAG TTA AGG ATC ACT TCG CAA TCC TTT    2966
Leu Asn Ile Gly Pro Asn Cys Lys Leu Arg Ile Thr Ser Gln Ser Phe
            70                  75                  80

GAA AAA ATC CAT AAC ACT GAA GAC GGG TTT GCT AGC AGA GAC ATG CAT    3014
Glu Lys Ile His Asn Thr Glu Asp Gly Phe Ala Ser Arg Asp Met His
            85                  90                  95

ATC GTT GTG GGG GAA AAC GCT TTT TTA GAC TTC GCG CCC TTC CCG TTA    3062
Ile Val Val Gly Glu Asn Ala Phe Leu Asp Phe Ala Pro Phe Pro Leu
            100                 105                 110

ATC CCC TTT GAA AAC GCG CAT TTT AAG GGC AAT ACC ACG ATT TCT TTG    3110
Ile Pro Phe Glu Asn Ala His Phe Lys Gly Asn Thr Thr Ile Ser Leu
115                 120                 125                 130

CGC TCT AGC TCC CAA TTG CTC TAT AGT GAA ATC ATT GTC GCA GGG CGA    3158
Arg Ser Ser Ser Gln Leu Leu Tyr Ser Glu Ile Ile Val Ala Gly Arg
```

```
                         135                 140                   145
GTG GCG CGC AAT GAG TTG TTT AAA TTC AAC CGC TTG CAC ACC AAA ATC                3206
Val Ala Arg Asn Glu Leu Phe Lys Phe Asn Arg Leu His Thr Lys Ile
            150                 155                 160

TCT ATT TTA CAA GAT GAG AAA CCC ATC TAT TAT GAC AAC ACG ATT TTA                3254
Ser Ile Leu Gln Asp Glu Lys Pro Ile Tyr Tyr Asp Asn Thr Ile Leu
            165                 170                 175

GAT CCC AAA ACC ACC GAC TTA AAT AAC ATG TGC ATG TTT GAT GGC TAT                3302
Asp Pro Lys Thr Thr Asp Leu Asn Asn Met Cys Met Phe Asp Gly Tyr
            180                 185                 190

ACG CAT TAT TTG AAT TTG GTG CTG GTC AAT TGC CCC ATA GAG CTG TCT                3350
Thr His Tyr Leu Asn Leu Val Leu Val Asn Cys Pro Ile Glu Leu Ser
195             200                 205                 210

GGC GTG CGA GGA TTG ATT GAA GAG AGC GAA GGA GTG GAT GGA GCC GTG                3398
Gly Val Arg Gly Leu Ile Glu Glu Ser Glu Gly Val Asp Gly Ala Val
                215                 220                 225

AGT GAA ATC GCT AGT TCT CAT TTA TGC CTG AAA GCT TTA GCG AAA GGC                3446
Ser Glu Ile Ala Ser Ser His Leu Cys Leu Lys Ala Leu Ala Lys Gly
            230                 235                 240

TCA GAA CCC TTG TTG CAT TTA AGA GAA AAA ATC GCT CGC TTT ATC ACG                3494
Ser Glu Pro Leu Leu His Leu Arg Glu Lys Ile Ala Arg Phe Ile Thr
            245                 250                 255

CAA ACG ATT ACG CCA AAG GTT TAAAAAACAC TTTAAAAAAG ATTATACCCT                   3545
Gln Thr Ile Thr Pro Lys Val
            260             265

TTAGTCTTTT TTAA                                                                3559

(2) INFORMATION FOR SEQ ID NO:2:

(i) SEQUENCE CHARACTERISTICS:
          (A) LENGTH: 5 amino acids
          (B) TYPE: amino acid
          (D) TOPOLOGY: linear (ii) MOLECULE TYPE: protein (xi) SEQUENCE DESCRIPTION: SEQ ID NO:2:

Leu Phe Ser Ile Phe
1               5

(2) INFORMATION FOR SEQ ID NO:3:

(i) SEQUENCE CHARACTERISTICS:
          (A) LENGTH: 195 amino acids
          (B) TYPE: amino acid
          (D) TOPOLOGY: linear (ii) MOLECULE TYPE: protein (xi) SEQUENCE DESCRIPTION: SEQ ID NO:3:

Met Leu Gly Leu Val Leu Leu Tyr Val Gly Ile Val Leu Ile Ser Asn
1               5                   10                  15

Gly Ile Cys Gly Leu Thr Lys Val Asp Pro Lys Ser Thr Ala Val Met
            20                  25                  30

Asn Phe Phe Val Gly Gly Leu Ser Ile Ile Cys Asn Val Val Val Ile
        35                  40                  45

Thr Tyr Ser Ala Leu Asn Pro Thr Ala Pro Val Glu Gly Ala Glu Asp
    50                  55                  60

Ile Ala Gln Val Ser His His Leu Thr Asn Phe Tyr Gly Pro Ala Thr
65                  70                  75                  80

Gly Leu Leu Phe Gly Phe Thr Tyr Leu Tyr Ala Ala Ile Asn His Thr
                85                  90                  95
```

```
Phe Gly Leu Asp Trp Arg Pro Tyr Ser Trp Tyr Ser Leu Phe Val Ala
            100                 105                 110

Ile Asn Thr Ile Pro Ala Ala Ile Leu Ser His Tyr Ser Asp Met Leu
            115                 120                 125

Asp Asp His Lys Val Leu Gly Ile Thr Glu Gly Asp Trp Trp Ala Ile
            130                 135                 140

Ile Trp Leu Ala Trp Gly Val Leu Trp Leu Thr Ala Phe Ile Glu Asn
145                 150                 155                 160

Ile Leu Lys Ile Pro Leu Gly Lys Phe Thr Pro Trp Leu Ala Ile Ile
                165                 170                 175

Glu Gly Ile Leu Thr Ala Trp Ile Pro Ala Trp Leu Leu Phe Ile Gln
            180                 185                 190

His Trp Val
        195

(2) INFORMATION FOR SEQ ID NO:4:

(i) SEQUENCE CHARACTERISTICS:
        (A) LENGTH: 170 amino acids
        (B) TYPE: amino acid
        (D) TOPOLOGY: linear (ii) MOLECULE TYPE: protein (xi) SEQUENCE DESCRIPTION: SEQ ID NO:4:

Met Ile Ile Glu Arg Leu Ile Gly Asn Leu Arg Asp Leu Asn Pro Leu
1               5                   10                  15

Asp Phe Ser Val Asp Tyr Val Asp Leu Glu Trp Phe Glu Thr Arg Lys
            20                  25                  30

Lys Ile Ala Arg Phe Lys Thr Arg Gln Gly Lys Asp Ile Ala Val Arg
            35                  40                  45

Leu Lys Asp Ala Pro Lys Leu Gly Phe Ser Gln Gly Asp Ile Leu Phe
50                  55                  60

Lys Glu Glu Lys Glu Ile Ile Ala Val Asn Ile Leu Asp Ser Glu Val
65                  70                  75                  80

Ile His Ile Gln Ala Lys Ser Val Ala Glu Val Ala Lys Ile Cys Tyr
            85                  90                  95

Glu Ile Gly Asn Arg His Ala Ala Leu Tyr Tyr Gly Glu Ser Gln Phe
            100                 105                 110

Glu Phe Lys Thr Pro Phe Glu Lys Pro Thr Leu Ala Leu Leu Glu Lys
            115                 120                 125

Leu Gly Val Gln Asn Arg Val Leu Ser Ser Lys Leu Asp Ser Lys Glu
            130                 135                 140

Arg Leu Thr Val Ser Met Pro His Ser Glu Pro Asn Phe Lys Val Ser
145                 150                 155                 160

Leu Ala Ser Asp Phe Lys Val Val Met Lys
                165                 170

(2) INFORMATION FOR SEQ ID NO:5:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO:5:

Met Asp Lys Gly Lys Ser Val Lys Ser Ile Glu Lys Ser Val Gly Met
```

|   1          |              |     5        |              |              |              |     10       |              |              |              |     15       |              |              |
|--------------|--------------|--------------|--------------|--------------|--------------|--------------|--------------|--------------|--------------|--------------|--------------|--------------|

Leu Pro Lys Thr Pro Lys Thr Asp Ser Asn Ala His Val Asp Asn Glu
                20                      25                      30

Phe Leu Ile Leu Gln Val Asn Asp Ala Val Phe Pro Ile Gly Ser Tyr
            35                      40                      45

Thr His Ser Phe Gly Leu Leu Ala Arg Asn Leu His Pro Ala Lys Lys
        50                      55                      60

Val Thr Asn Lys Glu Ser Ala Leu Lys Tyr Leu Lys Ala Asn Leu Ser
 65                     70                      75                      80

Ser Gln Phe Leu Tyr Thr Glu Met Leu Ser Leu Lys Leu Thr Tyr Glu
                    85                      90                      95

Ser Ala Leu Gln Gln Asp Leu Lys Arg Ile Leu Gly Val Glu Glu Ile
                100                     105                     110

Ile Thr Leu Ser Thr Ser Pro Met Glu Leu Arg Leu Ala Asn Gln Lys
        115                     120                     125

Leu Gly Asn Arg Phe Ile Lys Thr Leu Gln Ala Met Asn Glu Leu Asp
130                     135                     140

Ile Gly Ala Phe Phe Asn Ala Tyr Ala Gln Gln Thr Glu Asp Pro Thr
145                     150                     155                     160

His Ala Thr Ser Tyr Gly Val Phe Ala Ala Ser Leu Gly Ile Glu Leu
                165                     170                     175

Lys Lys Ala Leu Arg His Tyr Leu Tyr Ala Gln Thr Ser Asn Met Val
                180                     185                     190

Ile Asn Cys Val Lys Ser Val Pro Leu Ser Gln Asn Asp Gly Gln Lys
            195                     200                     205

Ile Leu Leu Ser Leu Gln Ser Pro Phe Asn Gln Leu Ile Glu Lys Thr
        210                     215                     220

Leu Glu Leu Asp Glu Ser His Leu Cys Ala Ala Ser Val Gln Asn Asp
225                     230                     235                     240

Ile Lys Ala Met Gln His Glu Ser Leu Tyr Ser Arg Leu Tyr Met Ser
                245                     250                     255

(2) INFORMATION FOR SEQ ID NO:6:

(i) SEQUENCE CHARACTERISTICS:
        (A) LENGTH: 199 amino acids
        (B) TYPE: amino acid
        (D) TOPOLOGY: linear (ii) MOLECULE TYPE: protein (xi) SEQUENCE DESCRIPTION: SEQ ID NO:6:

Met Val Lys Ile Gly Val Cys Gly Pro Val Gly Ser Gly Lys Thr Ala
 1                       5                      10                      15

Leu Ile Glu Ala Leu Thr Arg His Met Ser Lys Asp Tyr Asp Met Ala
                20                      25                      30

Val Ile Thr Asn Asp Ile Tyr Thr Lys Glu Asp Ala Glu Phe Met Cys
            35                      40                      45

Lys Asn Ser Val Met Pro Arg Glu Arg Ile Ile Gly Val Glu Thr Gly
        50                      55                      60

Gly Cys Pro His Thr Ala Ile Arg Glu Asp Ala Ser Met Asn Leu Glu
 65                     70                      75                      80

Ala Val Glu Glu Met His Gly Arg Phe Pro Asn Leu Glu Leu Leu Leu
                85                      90                      95

Ile Glu Ser Gly Gly Ser Asn Leu Ser Ala Thr Phe Asn Pro Glu Leu
                100                     105                     110

```
Ala Asp Phe Thr Ile Phe Val Ile Asp Val Ala Glu Gly Asp Lys Ile
        115                 120                 125

Pro Arg Lys Gly Gly Pro Gly Ile Thr Arg Ser Asp Leu Leu Val Ile
130                 135                 140

Asn Lys Ile Asp Leu Ala Pro Tyr Val Gly Ala Asp Leu Lys Val Met
145                 150                 155                 160

Glu Arg Asp Ser Lys Lys Ile Ala Ala Lys Ser Pro Leu Phe Leu Pro
                165                 170                 175

Asn Ile Arg Ala Lys Glu Gly Leu Asp Asp Val Ile Ala Trp Ile Lys
            180                 185                 190

Arg Asn Ala Leu Leu Glu Asp
            195
```

(2) INFORMATION FOR SEQ ID NO:7:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO:7:

```
Met Asn Thr Tyr Ala Gln Glu Ser Lys Leu Arg Leu Lys Thr Lys Ile
1               5                   10                  15

Gly Ala Asp Gly Arg Cys Val Ile Glu Asp Asn Phe Phe Thr Pro Pro
            20                  25                  30

Phe Lys Leu Met Ala Pro Phe Tyr Pro Lys Asp Asp Leu Ala Glu Ile
                35                  40                  45

Met Leu Leu Ala Val Ser Pro Gly Leu Met Lys Gly Asp Ala Gln Asp
    50                  55                  60

Val Gln Leu Asn Ile Gly Pro Asn Cys Lys Leu Arg Ile Thr Ser Gln
65                  70                  75                  80

Ser Phe Glu Lys Ile His Asn Thr Glu Asp Gly Phe Ala Ser Arg Asp
                85                  90                  95

Met His Ile Val Val Gly Glu Asn Ala Phe Leu Asp Phe Ala Pro Phe
                100                 105                 110

Pro Leu Ile Pro Phe Glu Asn Ala His Phe Lys Gly Asn Thr Thr Ile
                115                 120                 125

Ser Leu Arg Ser Ser Ser Gln Leu Leu Tyr Ser Glu Ile Ile Val Ala
            130                 135                 140

Gly Arg Val Ala Arg Asn Glu Leu Phe Lys Phe Asn Arg Leu His Thr
145                 150                 155                 160

Lys Ile Ser Ile Leu Gln Asp Glu Lys Pro Ile Tyr Tyr Asp Asn Thr
                165                 170                 175

Ile Leu Asp Pro Lys Thr Thr Asp Leu Asn Asn Met Cys Met Phe Asp
                180                 185                 190

Gly Tyr Thr His Tyr Leu Asn Leu Val Leu Val Asn Cys Pro Ile Glu
            195                 200                 205

Leu Ser Gly Val Arg Gly Leu Ile Glu Glu Ser Glu Gly Val Asp Gly
    210                 215                 220

Ala Val Ser Glu Ile Ala Ser Ser His Leu Cys Leu Lys Ala Leu Ala
225                 230                 235                 240

Lys Gly Ser Glu Pro Leu Leu His Leu Arg Glu Lys Ile Ala Arg Phe
                245                 250                 255

Ile Thr Gln Thr Ile Thr Pro Lys Val
                260                 265
```

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:8:

GCGAAAATAT GCTATGAAAT AGGAAACCGC CAT                           33

(2) INFORMATION FOR SEQ ID NO:9:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (xi) SEQUENCE DESCRIPTION: SEQ ID NO:9:

Ala Lys Ile Cys Tyr Glu Ile Gly Asn Arg His
1               5                   10

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: modified_base
        (B) LOCATION: 16
        (D) OTHER INFORMATION: /note= "W is either A or T."

(xi) SEQUENCE DESCRIPTION: SEQ ID NO:10:

TGGYAYRNNN NYYGCW                                                16

(2) INFORMATION FOR SEQ ID NO:11:

(i) SEQUENCE CHARACTERISTICS:
        (A) LENGTH: 6 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:11:

TTGACA                                                                     6

(2) INFORMATION FOR SEQ ID NO:12:

(i) SEQUENCE CHARACTERISTICS:
        (A) LENGTH: 6 base pairs
        (B) TYPE: nucleic acid
        (C) STRANDEDNESS: unknown
        (D) TOPOLOGY: unknown -continued (ii) MOLECULE TYPE: DNA (genomic)

(xi) SEQUENCE DESCRIPTION: SEQ ID NO:12:

TATAAT  6